(12) United States Patent
Jung

(10) Patent No.: US 6,423,871 B1
(45) Date of Patent: Jul. 23, 2002

(54) EFFICIENT SYNTHESIS OF SECONDARY AMINES BY SELECTIVE ALKYLATION OF PRIMARY AMINES

(75) Inventor: Kyung Woon Jung, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 09/513,219

(22) Filed: Feb. 25, 2000

Related U.S. Application Data

(60) Provisional application No. 60/121,867, filed on Feb. 26, 1999, provisional application No. 60/126,108, filed on Mar. 25, 1999, and provisional application No. 60/138,655, filed on Jun. 14, 1999.

(51) Int. Cl.$^7$ .............................................. C07C 211/00
(52) U.S. Cl. ..................... 564/384; 564/386; 564/404; 564/445; 564/459; 564/481; 560/155
(58) Field of Search ................................ 564/384, 386, 564/404, 445, 459, 481; 560/155

(56) References Cited

FOREIGN PATENT DOCUMENTS

JP 02202855 * 8/1990

* cited by examiner

Primary Examiner—Samuel Barts
(74) Attorney, Agent, or Firm—Gilberto M. Villacorta; Corinne M. Pouliquen; Katten Muchin Zavis

(57) ABSTRACT

A method for selective mono-N-alkylation of primary amines to produce secondary amines that are substantially free of overalkylated tertiary amines and quaternary ammonium salts, under mild reaction conditions without the necessity of protecting groups. Compounds of the class of secondary amines are produced by reacting an alkyl halide with an alkyl amine in anhydrous solvent, preferably dimethyl sulfoxide or N,N-dimethylformamide, in the presence of 0.1 to 3 molar equivalents of a cesium base. Optionally, the extent and selectivity of mono-N-alkylation is enhanced by addition to the reaction mixture of a powdered molecular sieve material for removal of water produced by the reaction, and/or tetrabutylammonium iodide to promote halide exchange. The invention permits selective and efficient mono-N-alkylation of a wide variety of substrates at 23° C.; does not cause racemization when used with enantiomerically-pure chiral substrates such as L-α-aminoesters; and is applied to solid phase synthesis whereby either the alkyl amine or alkyl halide is immobilized. The method is additionally used to produce polyamines, such as N-(2-(2-aminoethylthio)ethyl)ethylenediamine in 73% yield.

22 Claims, 7 Drawing Sheets

B. Electrophiles: Alkyl Halides, Alkyl Sulfonates, and Silyl Halides

C. Electrophiles: Bromide, Sulfonate from Alcohol (One Pot Conversion)

Alkylation of Primary Amine

Alkylation of Amino Esters

Alkylation of Amino Acid

EFFICIENT SYNTHESIS OF SECONDARY AMINES BY SELECTIVE ALKYLATION OF PRIMARY AMINES

RELATED APPLICATIONS

The present application claims priority to U.S. Provisional application 60/121,867, filed Feb. 26, 1999, U.S. Provisional application 60/126,108, filed Mar. 25, 1999, and U.S. Provisional application 60/138,655, filed Jun. 14, 1999 each of which is incorporated herein by reference in its respective entirety.

FIELD OF THE INVENTION

The present invention relates to the N-alkylation of organic nitrogen compounds containing a primary amine group and, in particular, to such N-alkylation performed by reacting an alkyl amine with an organic electrophile in the presence of a base catalyst under conditions such that substantially mono-N-alkylation of the alkyl amine occurs, resulting in a high yield of secondary amine.

BACKGROUND OF THE INVENTION

Secondary amines are widely used in the synthesis of numerous products including surfactants, textiles, agricultural products and medicines. Thus, an efficient means for the synthesis of secondary amines has long been sought. However, all the known direct alkylation methods give mainly over-alkylation products such as tertiary amines and quaternary ammonium salts instead of the desired secondary amines. See for example, M. S. Gibson, "The Chemistry of the Amino Group" (S. Patai, ed.), Interscience, 1968, p.45, and Mitsunobu, "Comprehensive Organic Chemistry", (H. D. Barton, ed.), Pergamon Press, 1979, 7:65.

The general scheme for production of secondary (2), tertiary (3) and quaternary (4) amines by successive N-alkylation reactions of primary amine (1) with an organic electrophile R'—X is as follows:

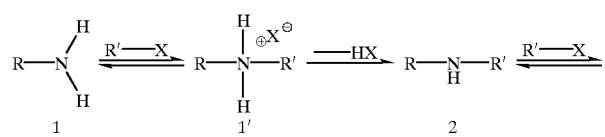
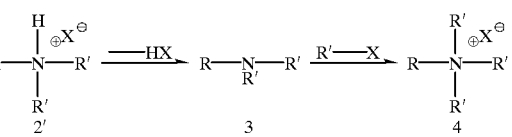

Because secondary amines are more nucleophilic than their corresponding primary amines, further alkylation to form tertiary (3) or quaternary (4) amines is thermodynamically favorable and difficult to suppress. Even with a limited amount of alkylating agent, the equilibriation of protonated dialkyl product (2') with the neutral primary amine (1) is sufficiently fast that a mixture of all alkylation products is obtained.

The resulting complex product mixture usually provides a low yield of secondary amine, and purification can be difficult. To avoid problems associated with overalkylation, reductive alkylation methods have been widely employed, wherein amines are reacted with aldehydes and the imine intermediates are reduced by sodium cyanoborohydride or a similar reductant to produce secondary amines, as described in: Szardenings et al. *J. Org. Chem.* (1996) 61:6720, and Klyuev & Khidekel, *Russian Chemical Rev.* (1980) 1:49. Depending on the choice of substrate, these methods typically give overalkylation products. In addition, aldehydes are usually unstable and expensive, limiting reactant availability, and reducing agents are both expensive and difficult to handle.

High temperatures are often required to achieve base-catalyzed direct N-alkylation. To minimize the need for harsh reaction conditions, activated reactants are frequently used. For example, U.S. Pat. No. 4,209,463 to Maender et al. discloses the use of activated formyl derivatives of aryl amines in the formation of nitrodiarylamines; U.S. Pat. No. 4,417,048 to Soula et al. describes N-alkylation of compounds bearing a labile hydrogen, and Fukuyama et al., *Tetrahedron Lett.* (1995) 36:6373 describes the use of 2,4-dinitrobenzenesulfonamides as activated N-alkylating agents.

Various additives that promote N-alkylation are known. These include phase-transfer catalysts, as described in Masse, *Synthesis* (1977) p.342; tertiary amine sequestering agents, as described in U.S. Pat. No. 4,417,048 to Soula et al.; and alkali cation exchange zeolites or molecular sieves, that improved selectivity of N-alkylation of aniline, as disclosed by Onaka et al., in *Chem. Lett.* (1982) 1783, and *J. Chem. Soc. Chem. Commun.* (1985) 1202. While these additives are effective in promoting certain specific N-alkylation reactions, there remains a need for reliable, efficient and generally-applicable N-alkylation procedures effective for a wide range of reactants, as required, for example, in the construction of peptidomimetic libraries, as discussed in Reichwein & Liskamp, *Tetrahedron Lett.* (1998) 39:1243.

Indirect methods of N-alkylation can provide substantially mono-N-alkylated products through the use of protecting groups that prevent further N-alkylation. See Fukuyarna et al., *Tetrahedron Lett.* (1995) 36:6373, and Croce et al., *J. Chem. Res.* (S) (1988) 347. These methods are of particular importance in the field of pharmaceuticals, see Sharm & Moniot "Isoquinoline Alkaloid Research" (1972), Plenum Press; solid phase synthesis, as described in Reichwein & Liskamp, *Tetrahedron Lett.* (1998) 39:1243 and Heinonen & Lonnberg, *Tetrahedron Lett.* (1997) 38:8569, and in the synthesis of peptidomimetic compounds such as N-alkylated peptides. After N-alkylation, the protecting group is removed to yield the secondary amine product. While the benefit of substantially mono-N-alkylation is achieved, and racemization of chiral centers is suppressed, additional synthetic steps and expense are required as compared to direct N-alkylation methods.

Therefore, there exists in this field a need for methods of simple, efficient N-alkylation of primary amines that yield substantially secondary amines, require only mildly reactive alkylating agents, such as alkyl bromides, which are generally more readily available than corresponding activated compounds, and can be performed under mild reaction conditions to minimize side reactions.

BRIEF SUMMARY OF THE INVENTION

It is therefore an object of the present invention to provide an improved process for mono-N-alkylation of primary alkyl amines which avoids the aforementioned disadvantages and drawbacks.

It is a further object of the present invention to provide a process that obviates harsh reaction conditions, suppresses over-alkylation, and avoids the use of protecting groups.

It is a further object of the present invention to provide a process characterized by reaction of an organic electrophile with a primary amine in the presence of a cesium base at mild temperatures.

It is a further object of the present invention to provide a process broadly comprising providing a cesium base catalyst, preferably CsOH or $Cs_2CO_3$, in an anhydrous solvent, and optionally including a molecular sieve for the removal of water and/or a halide-exchange promoting agent such as tetrabutyl ammonium iodide (TBAI).

It is a further object of the present invention to provide a process whereby unprotected primary amines are smoothly N-monoalkylated using more than one equivalent of alkylating agent in the presence of cesium hydroxide in DMF, giving rise to respectable yields and selectivity through an N-alkylation protocol that is direct, efficient and utilizes mild reaction conditions, and which can be exploited for other synthetic purposes.

These and other objects of the present invention will become obvious to those skilled in the art upon review of the following disclosure.

Disclosed herein is an efficient synthetic protocol for secondary alkyl amines, which can be generated by cesium hydroxide promoted N-alkylation of various primary alkyl amines with alkyl halides. Unlike the known methods, these protocols produce either mainly or exclusively secondary alkyl amines in high yields. All kinds of aliphatic amines are compatible with this technology and a variety of alkyl halides are readily incorporated to furnish dialkylamines efficiently. In a preferred embodiment, cesium hydroxide is used as a base in a catalytic amount when reactive halides such as benzyl bromide are employed. This catalytic process allows for the efficient and inexpensive preparation of various secondary amines essential to industrial and practical applications. The developed methodologies disclosed herewith are also believed to make significant contributions to the material sciences by providing new types of secondary amines in an economical fashion.

Thus a process providing a secondary amine of the general formula, R—NH—R', is disclosed wherein an organic electrophile, R—X, is reacted with a primary amine R'—$NH_2$ in an anhydrous solvent containing a cesium base in an amount sufficient to preferentially promote mono-N-alkylation of said primary amine by said organic electrophile, to provide a secondary amine. R and R' each comprise the same or a different hydrocarbon having one or more carbon atoms and X comprises a leaving group. The carbon atom covalently bonded to the leaving group and the carbon atom covalently bonded to the amine nitrogen atom are both saturated. The hydrocarbon has one or more carbon atoms. More preferably, the hydrocarbon has about 1–50 carbon atoms, and in a preferred embodiment, the hydrocarbon has about 1–30 carbons.

DETAILED DESCRIPTION OF THE INVENTION

Figure 1A:
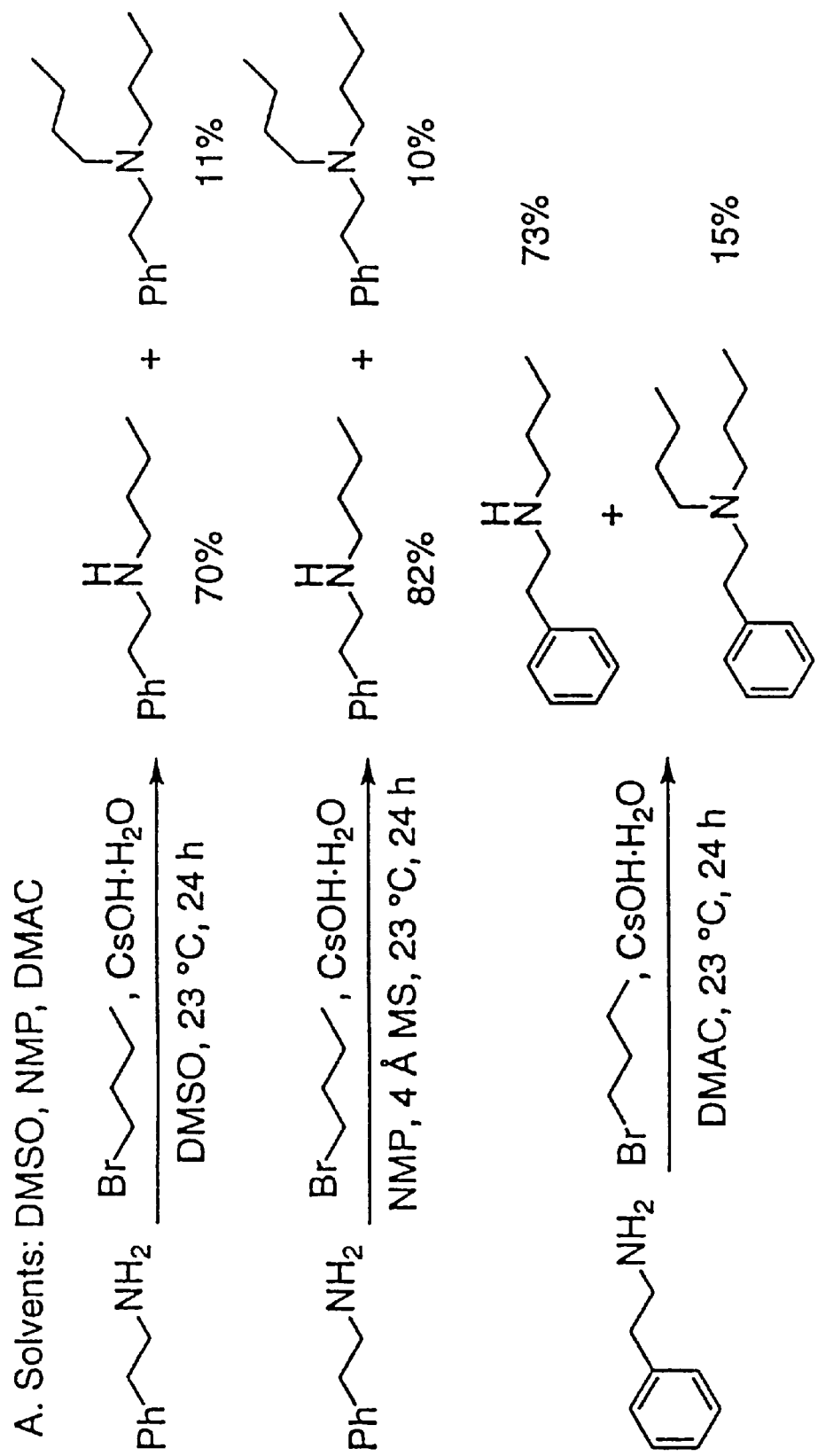
FIG. 1A illustrates the use of alternative solvents.

More particularly according to the present invention, one starting material is advantageously an organic nitrogen compound having the structural formula:

R—$NH_2$ in which R contains one or more saturated carbon atoms, one of which is covalently bonded to the primary amine nitrogen, and the R moieties comprise any substituents that are unreactive under the disclosed conditions of N-alkylation. It will be apparent to one skilled in the art that primary amines are sometimes referred to as mono-substituted amines in which the carbon adjacent to (bound to) the amine nitrogen is saturated. This saturated carbon may be a primary, secondary, or tertiary carbon, more preferably a secondary carbon, and most preferably a primary carbon. One of ordinary skill in the art would also appreciate that the primary amine of the present invention may have aliphatic hydrocarbons that are acyclic, cyclic, or polycyclic. Aliphatic aromatic hydrocarbons are also possible primary amine substrates of the instant invention, provided that aromatic substituent is not bonded directly to the amine nitrogen. Also, the secondary amine product of the present invention may at times be referred to as di-substituted amines, and that overalkylated tertiary or quaternary amines are sometimes referred to as tri-substituted or tetra-substituted amines, respectively.

The N-alkylating agent is an organic electrophile, having the structural formula:

$R_1$—X in which X is a halide and the $R_1$ moiety contains one or more saturated carbon atoms, one of which is covalently bonded to the halide, and the $R_1$ moieties comprise any substituents that are unreactive under the disclosed conditions of N-alkylation. It will be apparent to one skilled in the art that all organic electrophiles comprising unreactive $R_1$ moieties in which the carbon adjacent to the halide is saturated are included within this definition, which is herein designated as alkyl halide. The term organic electrophile includes organic halides such as chlorides, bromides, and iodides, as well as other organic electrophiles such as those containing mesyl (O-Ms) or tosyl (O-Ts) groups, silyl halides, or other organic compounds which are activated for electrophilic reaction. In preferred embodiments, chlorides and bromides are used. Most preferably, bromides are used.

The N-alkylation reaction is performed in an inert, anhydrous solvent, that also serves to regulate temperature, and which is preferably about 23° C. The anhydrous solvent is preferably dimethyl sulfoxide, N,N-dimethylformamide (DMF), 1-methyl-2-pyrrolidinone (NMP), N,N-dimethylacetamide (DMAC), or a mixture thereof. The most preferred anhydrous solvent is N,N-dimethylformamide. Other solvents can be used, including but not limited to acetonitrile, methylene chloride and toluene, but these tend to either cause the reaction not to go to completion, or to produce less selective mono-N-alkylation. An additional constraint upon the choice of solvent is that the cesium base must be adequately soluble within it.

The concentration of alkyl amine in the reaction is not critical and the preferred concentration is about 0.2 M.

Dilute solutions lead to a larger percentage of free anions, as discussed in Le Noble (1970) *Synthesis* 1:1. The preferred concentration of alkyl halide, relative to the concentration of alkyl amine, is between a slight excess and a several-fold excess. Suppression of further N-alkylation by the cesium base renders the concentration of alkyl halide non-critical. An advantage of the present invention is that efficient N-alkylation can be obtained with only a slight excess of alkyl halide, reducing expense and simplifying purification.

Preferred N-alkylating agents are those in which X is Cl, Br or I. The most preferred alkyl halides are those in which X is Br, in which case insolubility of CsBr produced by the N-alkylation reaction helps to drive the reaction to completion. Alkyl chlorides react more slowly, except in activated systems, but specific mono-N-alkylation is still obtained. Alkyl iodides react more slowly than alkyl bromides, and may be prone to elimination reactions.

The base in the present invention is chosen from cesium carbonate, cesium bicarbonate, and cesium hydroxide. The preferred base is CsOH, except where milder reaction conditions are advantageous, as in example 3, where cesium carbonate is preferred. The preferred amount of base, measured relative to alkyl amine concentration, is between 0.1 and 3. The higher concentrations of base are preferred for sterically-hindered alkyl amines, such as species 4, 6, and 13–15 of Table 1. The base concentration is easily optimized by one skilled in the art for a particular reaction.

Inclusion in the reaction of a powdered molecular sieve material, well known to those of skill in the art, for sequestering water produced by the N-alkylation reaction, is preferred, though not essential. In preferred embodiments, the pore size of the molecular sieve is 3–5 Å, and in the most preferred embodiments the pore size is 4 Å. The removal of water is believed to secure the amine from protonation and help drive the reaction to completion.

Optionally, TBAI can be included in the reaction in an amount roughly equimolar with the alkyl amine. TBAI accelerates N-alkylation of sterically-hindered secondary bromides.

Thus, in a preferred embodiment, the coupling of bromide (6) with in situ generated cesium amide (5) selectively forms the desired N-alkylated product (2) as shown:

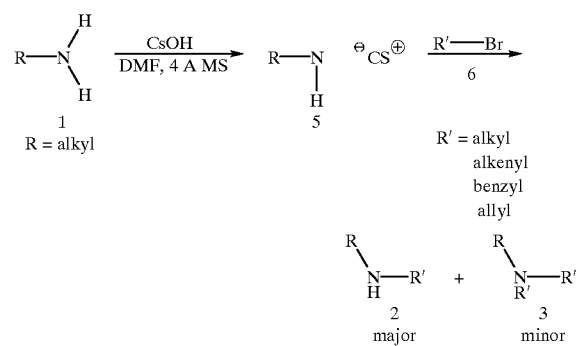

In order to further illustrate the present invention and the advantages thereof, the following specific examples are given, it being understood that same are intended only as illustrative and in no way limitative.

N-alkylations are initially studied using a limited amount of phenethylamine and a slight excess of 1-bromobutane. Several variables are considered such as variation in base, solvent, temperature, as well as the use of additives such as molecular sieves, acid scavengers, and phase transfer catalysts. Compared to cesium carbonate, bicarbonate, and fluoride and other alkali metal hydroxides, the preferred base is cesium hydroxide when using DMF, DMSO, NMP, or DMAC as the solvent. The preferred concentration of the amine in DMF is about 0.20 M.

EXAMPLE 1

The effect of cesium hydroxide and powdered 4 Å molecular sieve upon the N-alkylation of phenethylamine by bromobutane is tested. A flame dried 25-mL round-bottomed flask equipped with a magnetic stirring bar, rubber septum, and nitrogen inlet, is flushed with dry nitrogen and charged with activated powdered 4 Å molecular sieves (500 mg) and anhydrous DMF (8.3 mL). Under a nitrogen purge, cesium hydroxide monohydrate (0.28 g, 1.7 mmol) is added, and the mixture is stirred vigorously for 10 minutes. After phenethylamine (7) (0.21 mL, 1.7 mmol) is added, the mixture is stirred for an additional 30 minutes. By syringe, 1-bromobutane (8 (0.21 mL, 2.0 mmol) is added to the white suspension, which is stirred at room temperature for an additional 20 hours. The reaction mixture is then filtered to remove the molecular sieves and undissolved inorganic salts, and washed several times with ethyl acetate. After the filtrate is concentrated to a nominal volume by air, the residue is taken up in 1 N NaOH, and transferred to a 125 mL separatory funnel. The basic aqueous phase is extracted with ethyl acetate (4×20 ml), and the combined organic layers are washed with brine, dried over anhydrous sodium sulfate, filtered, and concentrated in vacuo to give a pale yellow oil.

The resulting crude mixture of products is separated and purified by silica gel column chromatography using a mixture of ethyl acetate-alcohol (9:1 v/v) as the eluting solvent. The common fractions are combined and evaporated to afford dialkylamine (2) (0.26 g, 1.5 mmol; 89%) as a colorless oil as well as trialkylamine (3) (0.04 g, 0.17 mmol; 10%) as a pale yellow oil.

Standard reaction conditions are as follows:

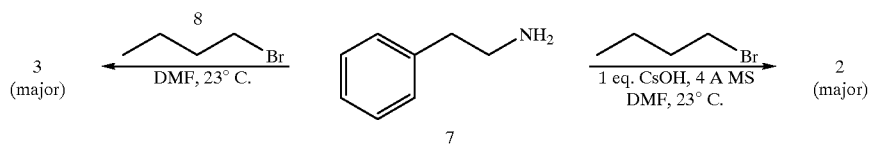

Changes from these standard reaction conditions in the following examples are as noted.

The yield of corresponding secondary dialkylamine moiety (2) and tertiary amines trialkylamine adduct (3) are 89% and 10%, respectively, in the presence of CsOH and molecular sieve, while in their absence 25% secondary amine (2) and 72% tertiary amine (3) are formed. Therefore, inclusion of cesium hydroxide and powdered 4 Å molecular sieve in the reaction promotes mono-N-alkylation over di-N-alkylation by a ratio of approximately 9:1, while in the absence of cesium hydroxide and molecular sieve, tertiary amine (3) is the major product.

Thus, in the absence of cesium base the tertiary amine/trialkylamine adduct is the predominant product, while in the presence of cesium base, the selectivity is reversed affording secondary amine/dialkylamine moiety.

EXAMPLE 2

Variations in the equivalents of cesium hydroxide are also investigated.

The optimum conditions for selective mono-N-alkylation of a variety of alkyl amines and alkyl bromides are summarized in Table 1 (infra). Conditions are optimized for CsOH concentration and reaction time. The temperature is room temperature, or about 23° C. and the alkyl bromide is present at slight excess (1.2 fold) compared to amine. Other reaction conditions are standard conditions as given in example 1.

In each example, the corresponding secondary amine is obtained in high yield, typically in 5–15 fold higher than the corresponding tertiary amine. Optimum CsOH concentrations ranged from 0.1 to 3 molar equivalents relative to alkyl amine: less CsOH is found to be required for activated bromides (benzyl and allyl systems), while 3 equivalents are preferred for sterically-hindered amines. Similarly, activated bromides require less reaction time for the reaction to complete than non-activated bromides.

Inclusion of certain additives are also found to be effective. Molecular sieves improve the selectivity and yield of the secondary amine. This manipulates the equilibrium by removing adventitious water that may retard the reaction rate. The addition of acid scavengers ($Et_3N$, DBU) or phase transfer catalysts ($Bu_4N^+HSO_4$) fail to enhance selectivity further. The presence of CsOH alone is enough to suppress amine protection. Tetrabutylammonium iodide assists in accelerating the monoalkylation of sterically hindered secondary bromides.

Several of the examples set forth represent alkyl amines containing a chiral center. The L-aminoesters are selectively mono-N-alkylated by three different alkyl bromides in high yield. Most significantly, racemization of the chiral center is not detected in any example: the chirality of the reactant's chiral center is preserved in the corresponding product. Even in the absence of protecting groups, better yields of the secondary amines of entries are obtained than were reported by Bowman & Coghlan, *Tetrahedron* (1997) 53:15787, using 2-nitrophenylsulfonyl protected L-valine methyl ester for alkylation. The absence of racemization in performing the present invention, and absence of protecting groups, is believed to be significant to biological applications in which enantiomeric purity is generally critical. For example, these results have tremendous implications in peptidomimetic synthesis.

Thus unprotected primary amines are smoothly N-monoalkylated using more than one equivalent of alkylating agent in the presence of cesium hydroxide in DMF, giving rise to respectable yields and selectivity.

TABLE 1

CsOH-Promoted N-Alkylation of Various Primary Amines $$R-NH_2 \xrightarrow[\text{4 Å MS, DMF, 23° C.}]{R'Br, CsOH \cdot H_2O} \underset{A}{R-\underset{H}{N}-R'} + \underset{B}{R-\underset{\underset{R'}{|}}{N}-R'}$$

| entry | $RNH_2$ | R'Br | Time | Yield (A) | Yield (B) |
|---|---|---|---|---|---|
| 1 | CH_3(CH_2)_6CH_2-NH_2 | CH_3(CH_2)_2CH_2-Br | 24 h | 93% | 0% |
| 2 | CH_3(CH_2)_6CH_2-NH_2 | Ph(CH_2)_3-Br | 22 h | 80% | 10% |
| 3 | Ph-CH_2-NH_2 | CH_3(CH_2)_4CH_2-Br | 22 h | 75% | 13% |
| 4 | Cyclohexyl-CH_2-NH_2 | Ph(CH_2)_3-Br | 22 h | 90% | 10% |
| 5 | Cyclopropyl-NH_2 | Ph(CH_2)_3-Br | 18 h | 83% | 12% |

TABLE 1-continued

CsOH-Promoted N-Alkylation of Various Primary Amines $$R-NH_2 \xrightarrow[4\text{ Å MS, DMF, 23° C.}]{R'Br,\ CsOH\cdot H_2O} \underset{A}{R-\underset{H}{N}-R'} + \underset{B}{R-\underset{R'}{\overset{R'}{N}}-R'}$$

| entry | RNH₂ | R'Br | Time | Yield (A) | Yield (B) |
|---|---|---|---|---|---|
| 6 | cyclooctyl-NH₂ | Ph(CH₂)₃Br | 22 h | 75% | 10% |
| 7 | t-Bu-NH₂ | Ph(CH₂)₃Br | 24 h | 90% | 0% |
| 8 | (2,4,4-trimethylpent-2-yl)-NH₂ | PhCH₂Br | 12 h | 87% | 0% |
| 9 | 1-adamantyl-NH₂ | PhCH=CHCH₂Br | 18 h | 66% | 0% |
| 10 | 2-adamantyl-NH₂ | Ph(CH₂)₃Br | 18 h | 82% | 0% |

TABLE 2

CsOH-Promoted N-Alkylation of Primary Amines with Various Bromides $$Ph\diagup\!\!\diagdown NH_2 \xrightarrow[4\text{ Å MS, DMF, 23° C.}]{R'Br,\ CsOH\cdot H_2O} \underset{A}{Ph\diagup\!\!\diagdown \underset{H}{\overset{H}{N}}\diagdown R'} + \underset{B}{Ph\diagup\!\!\diagdown \underset{R'}{\overset{R'}{N}}\diagdown R'}$$

| entry | R'Br (Bromide) | CsOH·H₂O | Time | Yield (A) | Yield (B) |
|---|---|---|---|---|---|
| 1 | CH₃CH₂CH₂CH₂Br | 1 eq | 21 h | 89% | 10% |
| 2 | Ph(CH₂)₃Br | 1 eq | 24 h | 85% | 10% |
| 3 | CH₂=CHCH₂Br | 0.1 eq | 4.5 h | 85% | 15% |
| 4 | PhCH₂Br | 0.1 eq | 4 h | 85% | 15% |
| 5 | (CH₃)₂CHCH₂Br | 3 eq | 24 h | 74% | 0% |

TABLE 2-continued

CsOH-Promoted N-Alkylation of Primary Amines with Various Bromides

Ph-CH$_2$CH$_2$-NH$_2$ + R'Br, CsOH·H$_2$O / 4 Å MS, DMF, 23° C. → Ph-CH$_2$CH$_2$-N(H)-R' (A) + Ph-CH$_2$CH$_2$-N(R')-R' (B)

| entry | R'Br (Bromide) | CsOH·H$_2$O | Time | Yield (A) | Yield (B) |
|---|---|---|---|---|---|
| 6 | sec-butyl Br | 3 eq | 48 h | 80% | 0% |
| 7 | isopropyl Br | 3 eq | 24 h | 70% | 0% |
| 8 | CH(Br)-CH(Me)-Et with CH$_2$NBn$_2$ | 1 eq | 36 h | 54% | 0% |
| 9 | CH(Br)-CH(CH$_2$Ph)-CH$_2$NBn$_2$ | 1 eq | 28 h | 45% | 0% |

TABLE 3

CsOH-Promoted N-Alkylation of Multifunctional Primary Amines

R—NH$_2$ + R'Br, CsOH·H$_2$O / 4 Å MS, DMF, 23° C. → R—N(H)—R' (A) + R—N(R')—R' (B)

| entry | RNH$_2$ | R'Br | Time | Yield (A) | Yield (B) |
|---|---|---|---|---|---|
| 1 | MeO-CH$_2$CH$_2$-NH$_2$ | Ph-(CH$_2$)$_3$-Br | 22 h | 84% | 15% |
| 2 | Cl$^{\ominus}$ H$_3$N$^{\oplus}$-CH(iPr)-CO$_2$Me | Ph-CH$_2$-Br | 4.5 h | 68% | 0% |
| 3 | Cl$^{\ominus}$ H$_3$N$^{\oplus}$-CH(iPr)-CO$_2$Me | CH$_2$=CH-(CH$_2$)$_3$-Br | 5 h | 61% | 0% |
| 4 | Cl$^{\ominus}$ H$_3$N$^{\oplus}$-CH(iPr)-CO$_2$Me | CH$_2$=CH-CH$_2$-Br | 10 h | 67% | 0% |
| 5 | H$_2$N-CH(iPr)-CH$_2$OH | Ph-CH$_2$-Br | 12 h | 74% | 0% |

TABLE 3-continued

CsOH-Promoted N-Alkylation of Multifunctional Primary Amines $$R-NH_2 \xrightarrow[\text{4 Å MS, DMF, 23° C.}]{R'Br, CsOH \cdot H_2O} \underset{A}{R-\underset{H}{\overset{}{N}}-R'} + \underset{B}{R-\underset{R'}{\overset{R'}{N}}-R'}$$

| entry | RNH₂ | R'Br | Time | Yield (A) | Yield (B) |
|---|---|---|---|---|---|
| 6 | (H₂N–CH(CH₂CH(CH₃)₂)–CH₂OH) | (Bn₂N–CH(CH(CH₃)CH₂CH₃)–CH₂Br) | 14 h | 60% | 0% |

EXAMPLE 3

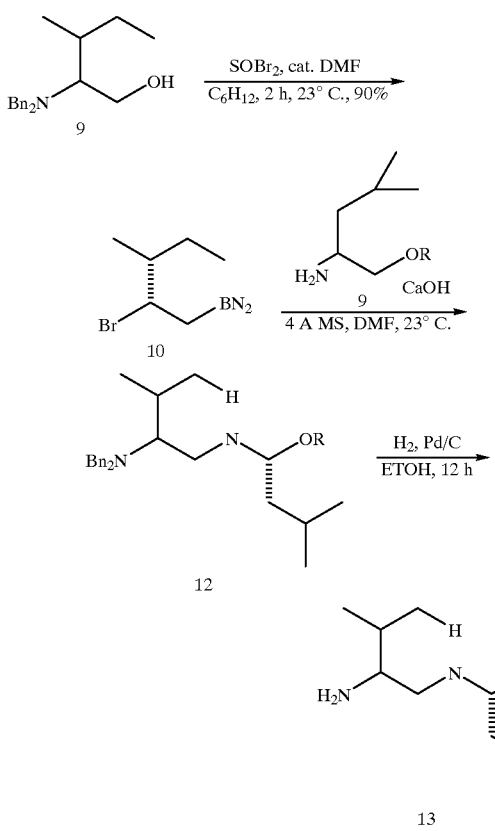

Peptidomimetic compounds of pharmaceutical interest can be prepared as secondary amines by N-alkylation, and such synthesis is frequently employed to generate libraries of compounds for activity screening. N-Alkylation for peptidomimetic synthesis is demonstrated using the present invention as shown in Table 2, by N-alkylation under standard reaction conditions of the L-leucine analog (11), in which the hydroxyl was optionally Bn-protected. Alkyl halide (10), an analog of L-isoleucine, is prepared in 90% yield by bromination of the corresponding alcohol (9) by treatment with thionyl bromide in benzene with catalytic N,N-dimethylformamide. N-Alkylation of (11) by (10) is performed under standard reaction conditions described above to produce the O-protected peptidomimetic (12). The N-alkylated, O-protected, secondary amine (12) is deprotected by catalytic hydrogenation over a palladium catalyst to yield the product peptidomimetic (13). In both cases (R=H and R=Bn, Table 2), N-alkylation yields more than 50% of the corresponding secondary amine.

TABLE 4

| R | 10 (Equiv) | 11 (Equiv) | Time (h) | 12 (Yield) | 13 (Yield) |
|---|---|---|---|---|---|
| H | 1.2 | 1 | 14 | 60 | 52 |
| Bn | 1.2 | 1 | 14 | 52 | 48 |

EXAMPLE 4

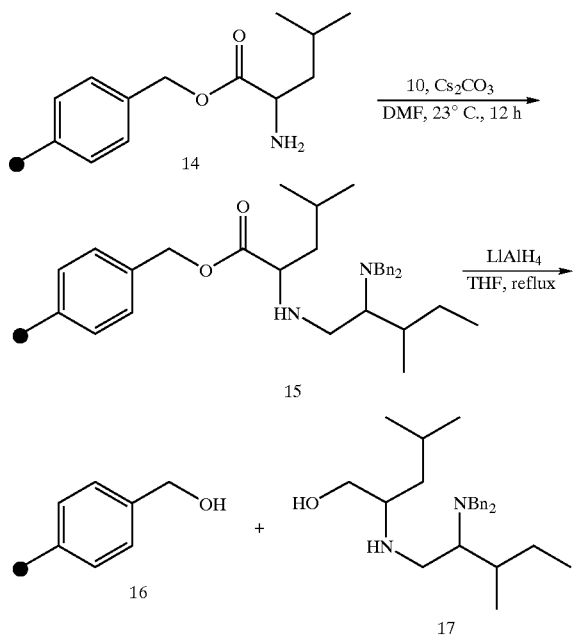

Solid phase synthesis of peptides, peptidomimetics and other bioactive compounds is widely used in the chemical and pharmaceutical industries. Solid phase N-alkylation using the present invention is performed by N-alkylation of (14), as shown in example 4, in which L-leucine is esterified to Merrifield resin by conventional methods known to those of skill in the art, to produce N-t-BOC-L-leucine (14). N-alkylation of N-t-BOC-L-leucine (14) by Bn$_2$-protected alkyl halide (10), an analog of L-isoleucine, yields the immobilized secondary amine (15). The N-alkylated secondary amine product (17) is cleaved from the resin in high yield by refluxing with lithium aluminum hydride in tetrahydrofuran. Cesium carbonate, a weaker base than cesium hydroxide, is used in this example to minimize premature cleavage from the resin.

EXAMPLE 5

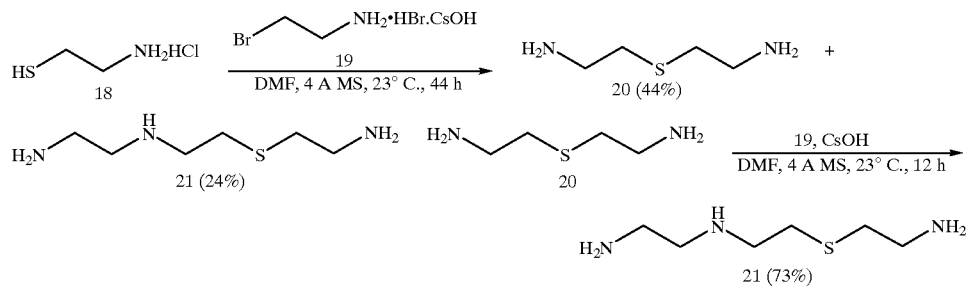

In embodiments of the present invention where the alkyl amine is a diamine or polyamine, or a diamine or polyamine is produced as an intermediate by the N-alkylation reaction, then polyamines can be produced by the present invention. N-Alkylation for synthesis of polyamine was demonstrated by synthesis of N-(2-(2-aminoethylthio)ethyl) ethylenediamine (21). For an alternative synthesis see U.S. Pat. No. 3,362,996 (1968) to Teumac, incorporated herein in its entirety by reference. 2-aminoethanethiol hydrochloride (18) is alkylated by 2-bromoethylamine hydrobromide (19 under standard conditions for 44 hours to yield diamine (20) and polyamine (21) in 44% and 24% yields, respectively. Diamine (20) is an intermediate in the synthesis of polyamine (21), and further alkylation for 12 hours under standard conditions results in N-alkylation of the remaining (20) to yield 73% N-(2-(2-aminoethylthio)ethyl) ethylenediamine (21).

EXAMPLE 6

Additional examples of the utility of the present invention in promoting N-alkylation of various primary amines are presented in Table 3. Entries 1–3 show that 75%, or better, yields of secondary amine can be obtained using mildly sterically crowded reagents such as branched alkanes, cyclooctane derivatives, or benzyl derivatives. Examples 4 and 5 demonstrate use of the present invention in the case of multifunctional primary amines: in both cases good yields of secondary amines were obtained, obviating the need for protecting groups for the hydroxyl groups and tryptopan side chain.

EXAMPLE 7

FIG. 1A illustrates the use of alternative solvents. Both DMSO, NMP and DMAC result in high yields of secondary amines in the presence of CsOH, with yields of secondary and tertiary amines only slightly inferior to those obtained using DMF (cf. Table 1, entry 1). Thus, while use of each of these solvents is acceptable, DMF is the preferred solvent.

Figure 1B:
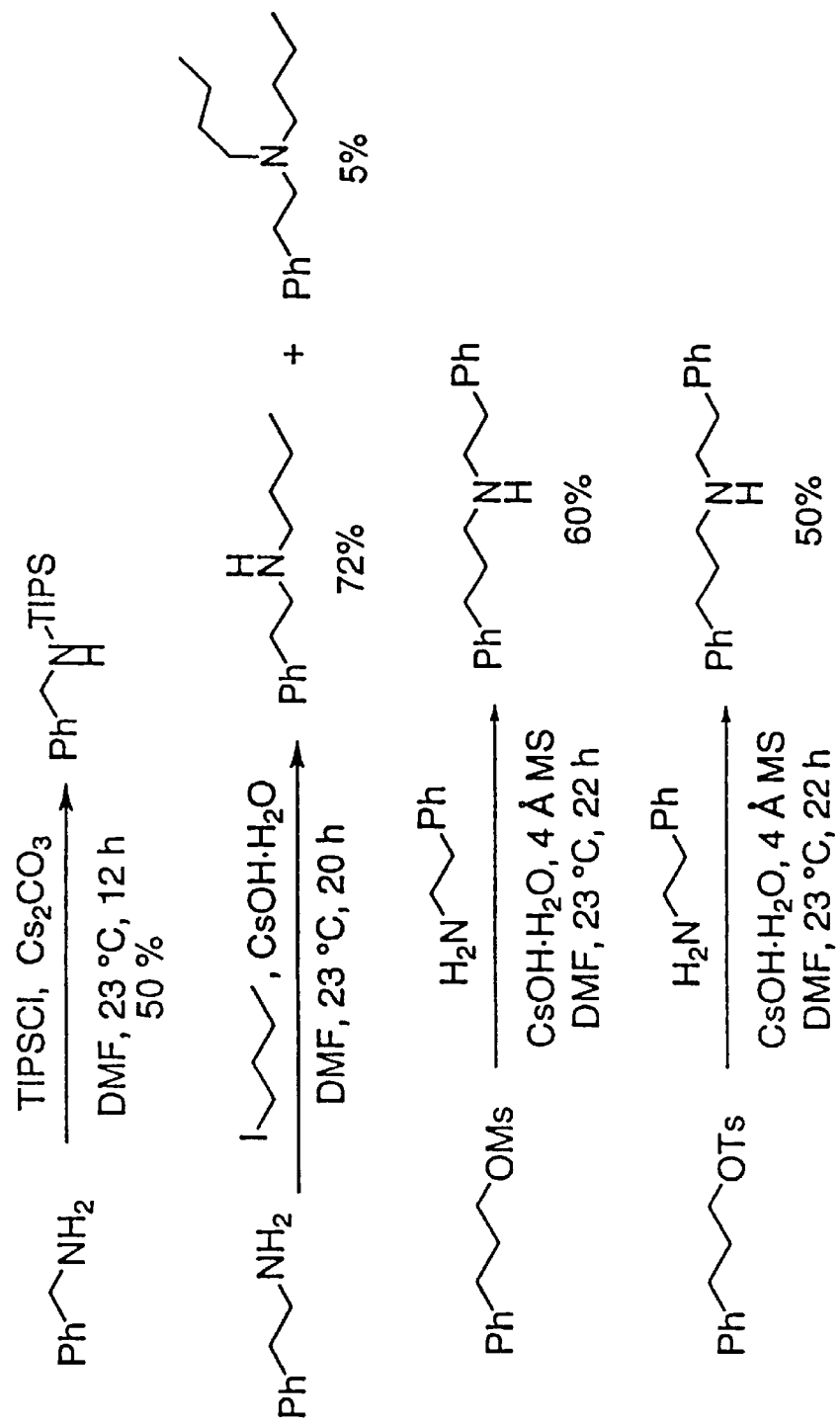
FIG. 1B illustrates N-alkylation of compounds containing alternative electrophiles to bromide.

FIG. 1B illustrates N-alkylation of compounds containing alternative electrophiles to bromide. Use of iodide in place of bromide generally yields a more sluggish reaction, slightly lower yield, and, carries an increased risk of undesired elimination side-reactions. Entries 2 and 3 demonstrate that O Ms and O Ts derivatives can also be N-alkylated by the present invention in moderate to good yields. As these functional groups are widely used in the art, this enhances the usefulness of the present invention for applications involving solid phase and/or peptidomimetic applications.

Figure 1C:
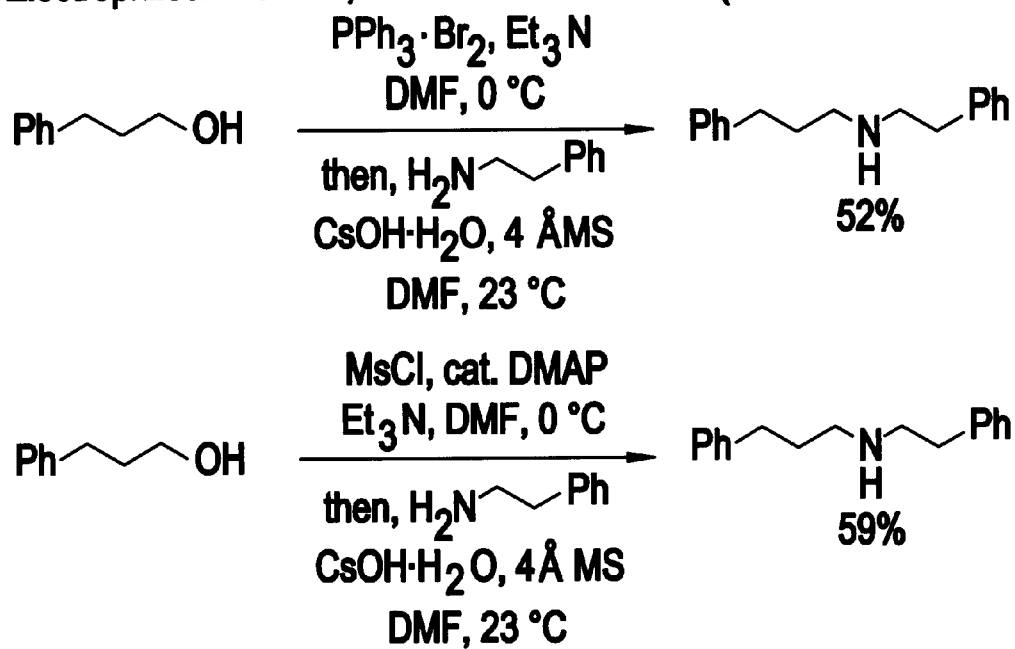
FIG. 1C illustrates obtaining a "one pot" N-alkylation of a suitable primary alcohol in the presence of suitable reagents.

FIG. 1C illustrates obtaining a "one-pot" N-alkylation of a suitable primary alcohol in the presence of suitable reagents. Bromination (example 1) or mesylation (example 2) of a primary alcohol is achieved by standard procedures and reagents in DMF, and subsequent addition of a primary amine to the same reaction mixtures results in good yields of the product corresponding to N-alkylation of the primary alcohol.

EXAMPLE 8

Figure 2:
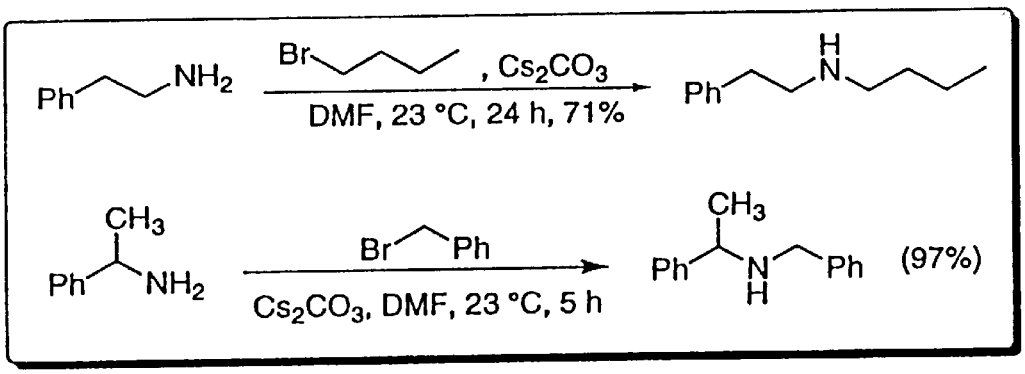
FIG. 2 illustrates the use of $Cs_2CO_3$ as a cesium base.
Figure 2:
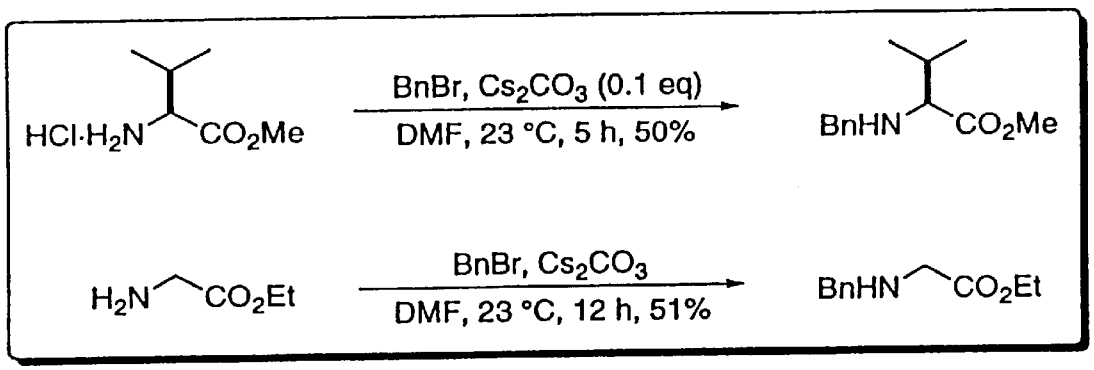
Figure 2:
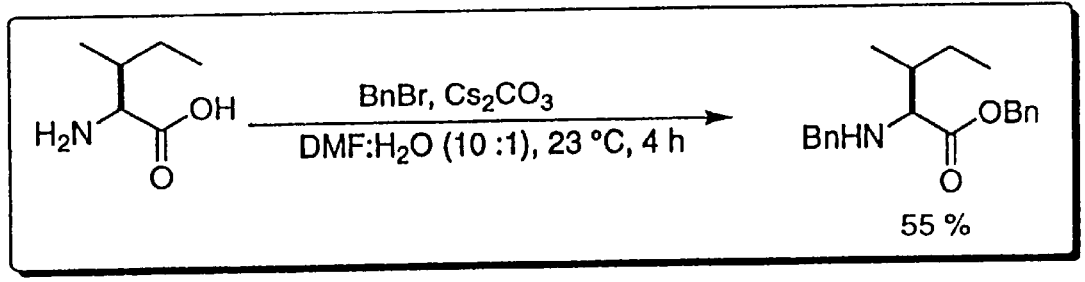

FIG. 2 illustrates an alternative embodiment of the present invention wherein Cs$_2$CO$_3$ is used in place of CsOH. Alkylation of a primary amine provides direct comparison with the use of CsOH, from which it can be seen that a lower yield (71%) of the secondary amine is obtained using Cs$_2$CO$_3$ in place of CsOH (89%). Despite the lower yield, using the milder Cs$_2$CO$_3$ in place of CsOH can be advantageous where other functional groups on the reagents are sensitive to CsOH. N-alkylation of sensitive amino esters is shown in the second set of examples in FIG. 2: good yields of the desired secondary amines are obtained with the ester group intact.

The third example of FIG. 2 illustrates combined N-alkylation and esterification in the presence of Cs$_2$CO$_3$ in place of CsOH and also where 10% (v/v) water is present.

EXAMPLE 9

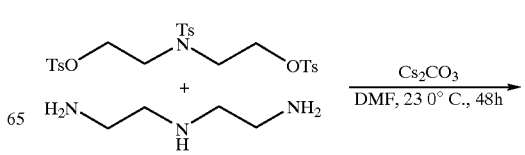

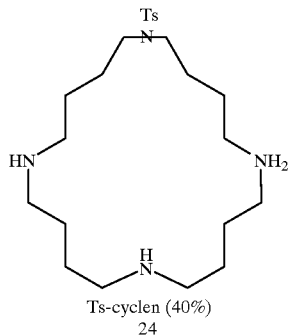

Ts-cyclen (40%)
24

Cyclic products can be easily obtained in the present invention through the use of bifunctional reagents. FIG. 9 illustrates synthesis of Ts-cyclen (24) from the corresponding triamine (23) and O-Ts protected dialcohol (22). The Ts-cyclen is a useful intermediate in the synthesis of metal-chelating cyclen derivatives for use as MRI imaging reagents.

EXAMPLE 10

Figure 3A:
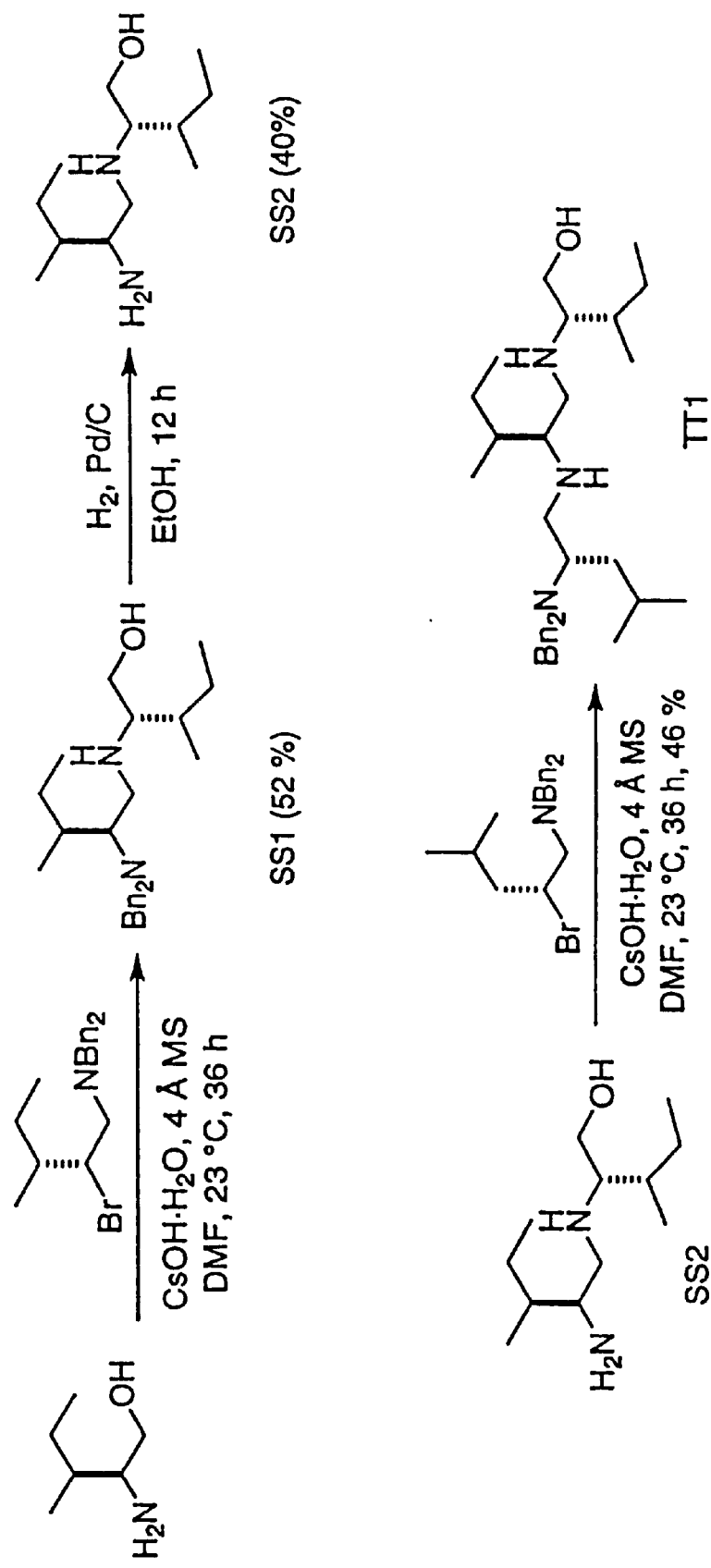
FIGS. 3A and 3B illustrate application of N-alkylation for peptidomimetic synthesis.
Figure 3B:
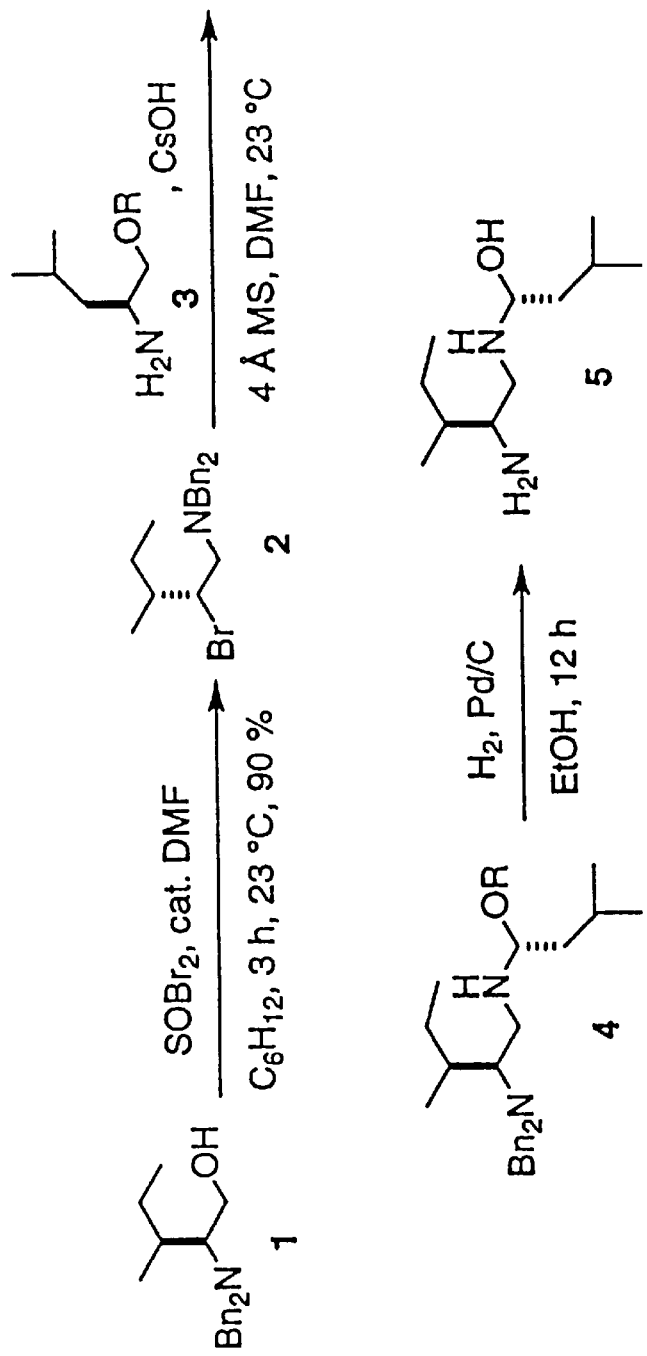

FIG. 3 illustrates a synthetic scheme for synthesis of the peptidomimetic tripeptide analogue of Leu-Ile-Leu. Following N-alkylation to form the Bn-protected dipeptide analogue of Ile-Ile, deprotection is achieved by catalytic hydrogenation, exposing the primary amine for further N-alkylation to produce the tripeptide analogue. Clearly, this cycle of N-alkylation and deprotection could be repeated to yield longer oligomeric peptidomimetic compounds.

EXAMPLE 11

Figure 4:
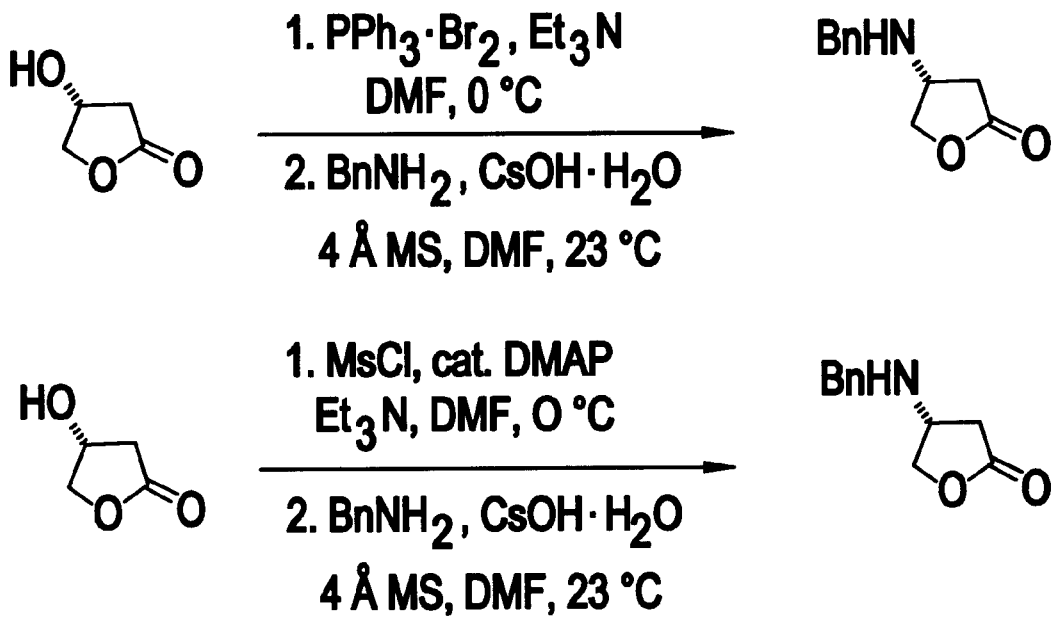
FIG. 4 illustrates N-alkylation of halogenated compounds resulting in secondary amine enantiomers.

FIG. 4 illustrates how the prior examples, in which N-alkylation is preceded by halogenation of the corresponding alcohol, can be exploited to control the stereochemistry of N-alkylation. Beginning from the identical stereoisomer of an alcohol, the stereochemistry of halogenation is controlled, through the choice of halogenation method, to provide either inversion (first method) or preservation (second method) of the chiral center. As demonstrated previously in Table 1, N-alkylation by the present invention proceeds with inversion of chirality. Therefore N-alkylation of the halogenated compounds in FIG. 4 results in both secondary amine enantiomers.

EXAMPLE 12

Preparation of Dialkylamine E1

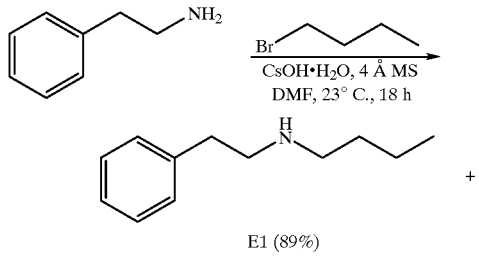

E1 (89%)

+

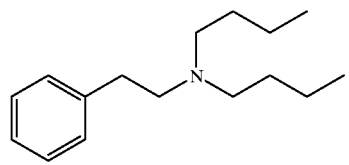

E2 (10%)

A flame dried 25 mL round-bottomed flask equipped with a magnetic stirring bar, rubber septum, and nitrogen inlet, is flushed with dry nitrogen and charged with activated powdered 4 Å molecular sieves (500 mg) and anhydrous DMF (8.3 mL). Under a nitrogen purge, cesium hydroxide monohydrate (280 mg, 1.7 mmol, 1 eq.) is added, and the mixture is vigorously stirred for 10 minutes. After phenethylamine (0.21 mL, 1.7 mmol, 1 eq.) is added, the mixture is stirred for an additional 30 minutes. By syringe, 1-bromobutane (0.21 mL, 2.0 mmol, 1.2 eq.) is added to the white suspension and the reaction is allowed to proceed at room temperature for 18 hours. The reaction mixture is then filtered to remove the molecular sieves and undissolved inorganic salts, and washed several times with ethyl acetate. After the filtrate is concentrated to a nominal volume by air, the residue is taken up in 1 N NaOH, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil.

The resulting crude mixture of products is separated and purified by silica gel column chromatography using a mixture of ethyl acetate-ethanol (9:1 v/v) as the eluting solvent. The common fractions are combined and evaporated to afford dialkylamine E1 (260 mg, 89%) as a colorless oil as well as trialkylamine E2 (40 mg, 10%) as a pale yellow oil. Data for E1: IR (thin film) 3290, 3063, 3027, 2956, 2872, 2815,1496, 1453, 1125, 748 cm$^{-1}$. $^1$H NMR (360 MHz, CDCl$_3$) δ 0.89 (t, J=7.4 Hz, 3 H), 1.25–1.35 (m, 2 H), 1.36–1.64 (m, 2 H), 1.75 (s, NH), 2.60 (t, J=7.0 Hz, 2 H), 2.49–2.69 (m, 2 H 2.77–2.92 (m, 2 H), 7.16–7.35 (m, 5 H). $^{13}$C NMR (90 MHz, CDCl$_3$) δ 13.78, 20.27, 31.82, 36.13, 49.33, 51.00, 125.88, 128.22, 128.47, 139.86. Data for E2: IR (thin film) 3026, 2930, 2871, 2861, 2800, 1453, 1100, 697 cm$^{-1}$. $^1$H NMR (360 MHz, CDCl$_3$) δ 0.89–0.98 (m, 6 H), 1.25–1.35 (m, 4 H), 1.40–1.53 (m, 4 H), 2.41–2.51 (m, 4 H), 2.67–2.75 (m, 4 H), 7.12–7.33 (m, 5 H). $^{13}$C NMR (90 MHz, CDCl$_3$) δ 14.08, 20.74, 29.29, 33.44, 53.80, 56.11, 125.80, 128.27, 128.69, 140.90.

EXAMPLE 13

Preparation of Dialkylamine F1

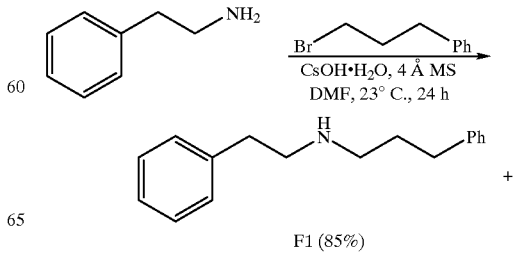

+

F1 (85%)

-continued

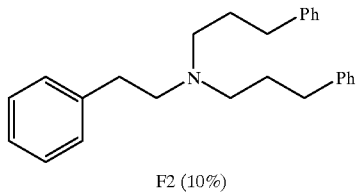

F2 (10%)

Under an atmosphere of nitrogen, activated 4 Å molecular sieves (500 mg) and cesium hydroxide monohydrate (280 mg, 1.65 mmol, 1 eq.) are placed in anhydrous N,N-dimethylformamide (8.3 mL). Phenethylamine (0.21 mL, 1.65 mmol, 1 eq.) is injected ten minutes later into the turbid solution and stirred for 30 minutes. 1-Bromo-3-phenylpropane (0.38 mL, 2.5 mmol, 1.5 eq.) is added to the solution by syringe and the reaction is allowed to proceed at room temperature under nitrogen for 24 hours. The reaction mixture is then filtered and the undissolved solids are washed with ethyl acetate. After the filtrate is concentrated to a nominal volume by blowing air, the residue is taken up in 1 N NaOH and extracted with ethyl acetate (3×30 mL). The organic layer is washed with water (3×30 mL), followed by brine (30 mL), and then dried using anhydrous sodium sulfate. Solvent is removed in vacuo and the residue is purified via flash column chromatography (9:1 EtOAc:EtOH) to yield the desired dialkylamine F1 (330 mg, 85%) as a clear oil and the trialkylamine F2 (60 mg, 10%) as a pale yellow oil. Data for F1: $^1$H NMR (360 MHz, CDCl$_3$) δ 1.55 (s, NH), 1.76–1.85 (m, 2 H), 2.59–2.67 (m, 4 H), 2.78–2.93 (m, 4 H), 7.06–7.31 (m, 10 H). $^{13}$C NMR (90 MHz, CDCl$_3$) δ 31.17 32.57, 34.41, 46.32, 48.28, 123.7, 124.01, 126.15, 136.73, 139.20. Data for F2: $^1$H NMR (360 MHz, CDCl$_3$) δ 1.76–1.89 (m, 4 H), 2.56 (t, J=7.1 Hz, 4 H), 2.65 (t, J=7.8 Hz, 4 H), 2.73 (s, 4 H), 7.18–7.31 (m, 15 H). $^{13}$C NMR (90 MHz, CDCl$_3$) δ 28.79, 33.39, 33.63, 53.33, 55.87, 125.64, 125.82, 128.23, 128.67, 140.68, 142.28.

EXAMPLE 14

Preparation of Dialkylamine G1

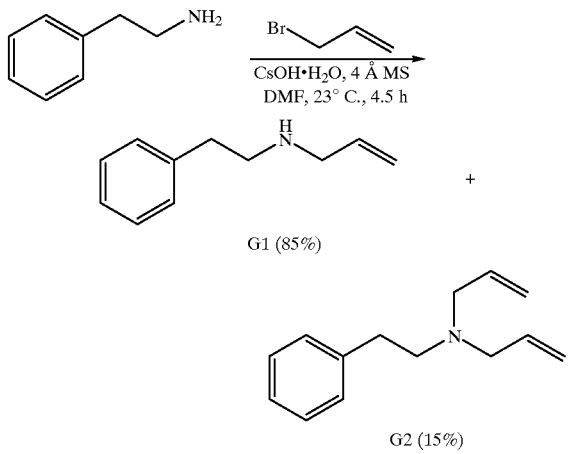

A flame dried 25 mL round-bottomed flask equipped with a magnetic stirring bar, rubber septum, and nitrogen inlet, is flushed with dry nitrogen and phenethylamine (0.21 mL, 1.7 mmol, 1 eq.), activated 4 Å molecular sieves (500 mg), and cesium hydroxide monohydrate (28 mg, 0.165 mmol, 0.1 eq.) are dissolved in anhydrous N,N-dimethylformamide (8.3 mL) and allowed to stir for 30 minutes at room temperature. Allyl bromide (0.17 mL, 2.0 mmol, 1.2 eq.) is added by syringe to the white suspension with vigorous stirring. The reaction is allowed to proceed at ambient temperature for 4.5 hours. The reaction suspension is then filtered, and rinsed with ethyl acetate. The filtrate is concentrated by blowing air, and the residue is dissolved in 1 N NaOH and extracted with ethyl acetate (3×30 mL). The organic layer is washed with water (2×30 mL), brine (30 mL), and dried over anhydrous sodium sulfate. Concentration of the solvent, and purification using flash column chromatography (9:1 EtOAc:EtOH) yields the desired dialkylamine G1 (220 mg, 85%) as a clear oil and the trialkylamine G2 (50 mg, 15%) as a yellow oil. Data for G1: IR (thin film) 3313, 3077, 3063, 2956, 2924, 2854, 2816, 1495, 1453, 918, 749 cm$^{-1}$. $^1$H NMR (360 MHz, CDCl$_3$) δ 2.07 (s, NH), 2.82–2.91 (m, 4H), 3.27(d,J=6.5 Hz, 2 H), 5.13 (m, 2 H), 5.88 (ddt, J=17, 10.3, 6 Hz, 1H), 7.18–7.31 (m, 5 H). $^{13}$C NMR (90 MHz, CDCl$_3$) δ 36.13, 50.32, 52.11, 116.19, 126.13, 128.25, 136.25, 139.80. Data for G2: $^1$H NMR (360 MHz, CDCl$_3$) δ 2.72–2.80 (m, 4 H), 3.20 (d, J=6.4 Hz, 4 H), 5.16 (m, 4 H), 5.86 (ddt, J=17.1, 10.4, 6Hz, 2 H), 7.17–7.30 (m, 5 H). $^{13}$C NMR (90 MHz, CDCl$_3$) δ 33.11, 55.00, 56.71, 117.55, 125.85, 128.25, 128.64, 135.41, 140.43.

EXAMPLE 15

Preparation of Dialkylamine H1

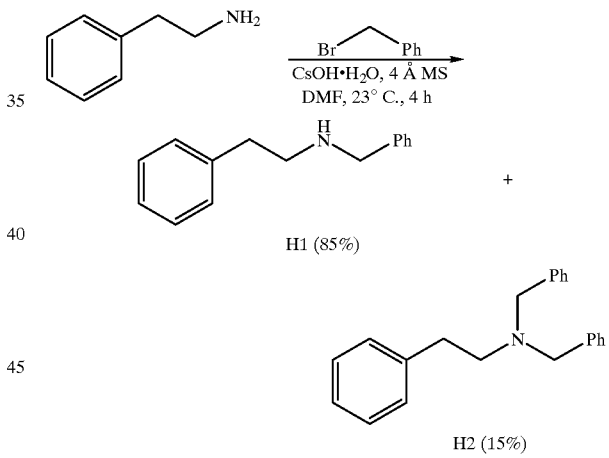

Under an atmosphere of nitrogen, activated 4 Å molecular sieves (500 mg), and cesium hydroxide monohydrate (30 mg, 0.165 mmol, 0.1 eq.) are placed in anhydrous N,N-dimethylformamide (8.2 mL). Phenethylamine (0.21 mL, 1.65 mmol, 1 eq.) is injected ten minutes later into the turbid solution and stirred for an additional 30 minutes. Benzyl bromide (0.22 mL, 1.8 mmol, 1.1 eq.) is added to the solution by syringe and the reaction is allowed to proceed at room temperature under nitrogen for 4 hours. The reaction mixture is then filtered to remove molecular sieves and undissolved inorganic salts and rinsed with ethyl acetate. After the filtrate is concentrated to a nominal volume by blowing air, the residue is taken up in 1 N NaOH and extracted with ethyl acetate (3×30 mL). The organic layer is washed with water (3×30 mL), followed by brine (30 mL), and then dried using anhydrous sodium sulfate. Solvent is removed in vacuo and the residue is purified via flash column chromatography (9:1 EtOAc:EtOH) to yield the desired dialkylamine H1 (290 mg, 85%) as a clear oil and the trialkylamine H2 (71 mg, 15%) as a pale yellow oil. Data for H1: IR (thin film) 3350, 3026, 2925, 2872, 2815, 1497, 1455, 696 cm$^{-1}$. $^1$H NMR (360 MHz, CDCl$_3$) δ 1.87 (s, NH), 2.72–2.92 (m, 4 H), 3.79 (s, 2 H), 7.07–7.49 (m, 10 H). $^{13}$C NMR (90 MHz, CDCl$_3$) δ 36.10, 50.33, 53.63, 126.10, 126.94, 128.10, 128.33, 128.39, 128.65, 139.80. Data for H2: $^1$H NMR (360 MHz, CDCl$_3$) δ 2.59–2.61 (m, 4 H), 3.52 (s, 4 H), 6.94–7.21 (m, 15 H). $^{13}$C NMR (90 MHz, CDCl$_3$) δ 33.26, 54.88, 57.98, 125.67, 126.69, 128.03, 128.19, 128.55, 128.66, 128.84, 139.9, 140.0.

EXAMPLE 16

Preparation of Dialkylamine I1

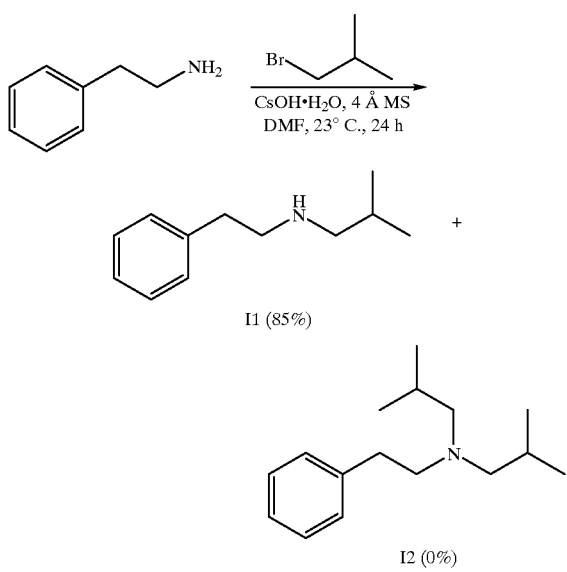

Into a solution of phenethylamine (0.21 mL, 1.65 mmol, 1 eq.) in anhydrous N,N-dimethylformamide (8.3 mL), are added successively activated 4 Å molecular sieves (500 mg), and cesium hydroxide monohydrate (910 g, 5.4 mmol, 3.2 eq.), then the resulting suspension is stirred under a nitrogen atmosphere for 30 minutes. By syringe, 1-bromo-2-methylpropane (0.42 mL, 4.0 mmol, 2.4 eq.) is added and the reaction is allowed to proceed under nitrogen for 24 hours at room temperature. The reaction mixture is then filtered to remove molecular sieves and undissolved inorganic salts, and rinsed several times with ethyl acetate. The combined filtrates are concentrated to a nominal volume by blowing air, and the residue is taken up in 1 N NaOH and extracted with ethyl acetate (3×30 mL). The organic layer is washed with water (2×30 mL), brine (30 mL), and dried over anhydrous sodium sulfate. The solvent is concentrated in vacuo and the residue is purified by flash column chromatography (9:1 EtOAc:EtOH) to give the desired dialkylamine I1 (220 mg, 74%) as a colorless oil. The trialkylamine I2 is not observed. Data for I1: $^1$H NMR (360 MHz, CDCl$_3$) δ 0.81 (d, J=6.5 Hz, 6 H), 1.22 (s, NH), 1.60–1.71 (m, 1 H), 2.36 (d, J=6.7 Hz, 2 H), 2.73–2.79 (m, 4 H), 6.99–7.24 (m, 5 H). $^{13}$C NMR (90 MHz, CDCl$_3$) δ 20.48, 28.08, 36.22, 51.14, 57.69, 125.90, 128.24, 128.57, 139.98.

EXAMPLE 17

Preparation of Dialkylamine J1

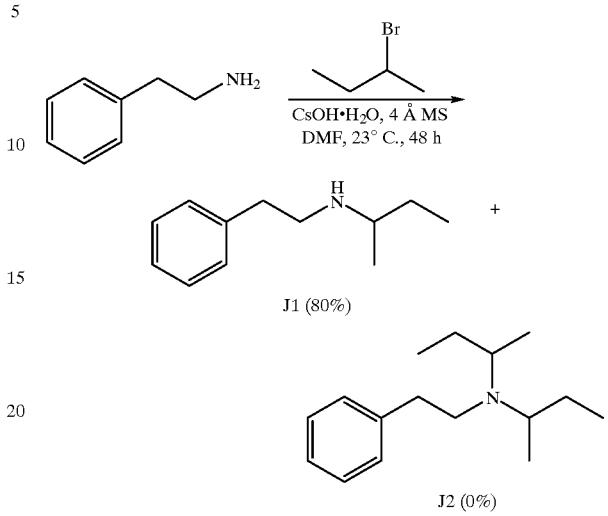

A flame dried 25 mL round-bottomed flask equipped with a magnetic stirring bar, rubber septum, and nitrogen inlet, is swept with dry nitrogen. Phenethylamine (0.21 mL, 1.7 mmol, 1 eq.), activatived 4 Å molecular sieves (500 mg), and cesium hydroxide monohydrate (690 mg, 4.1 mmol, 2.4 eq.) are dissolved in anhydrous N,N-dimethylformamide (8.3 ml) and allowed to stir for 30 minutes at room temperature. 2-Bromobutane (0.9 mL, 8.2 mmol, 5.0 eq.) is added by syringe to the white suspension with vigorous stirring. The reaction is allowed to proceed at ambient temperature for 48 hours. The reaction is then filtered and rinsed with ethyl acetate. The filtrate is concentrated by blowing air, and the residue is dissolved in 1 N NaOH, and extracted with ethyl acetate (3×30 mL). The organic layer is washed with water (2×30 mL), brine (30 mL), and dried over anhydrous sodium sulfate. Concentration of the solvent, and purification using flash column chromatography (9:1 EtOAc:EtOH) yields the desired dialkylamine Ji as a clear oil (230 mg, 80%) and the trialkylamine J2 is not observed. Data for J1: IR (thin film) 3306, 3084, 3061, 3025, 2931, 2855, 2810, 1495, 1457, 1125, 745 cm$^{-1}$. $^1$H NMR (360 MHz, CDCl$_3$) δ 0.82 (t, J=7.5 Hz, 3 H), 1.00 (d, J=6.1 Hz, 3 H), 1.24–1.31 (m, 2 H), 1.42–1.48 (m, 1 H), 2.51–2.56 (m, 1 H) 2.78–2.89 (m, 4 H), 7.12–7.39 (m, 5 H). $^{13}$C NMR (90 MHz, CDCl$_3$) δ 10.00, 19.54, 29.28, 35.35, 48.35, 54.21, 125.89, 128.21, 128.45, 139.91.

EXAMPLE 18

Preparation of Dialkylamine K1

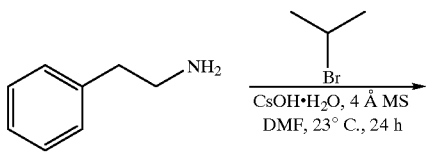

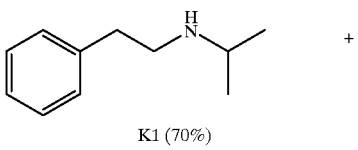

K1 (70%)

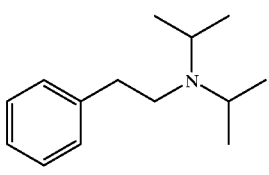

K2 (0%)

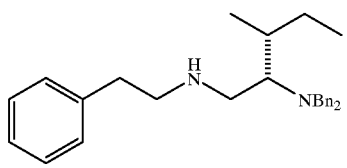

Y1 (54%)

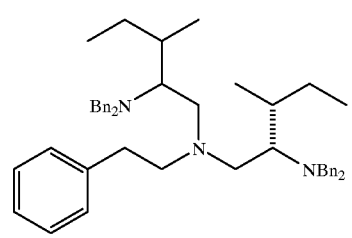

Y2 (0%)

A flame dried 25 mL round-bottomed flask equipped with a magnetic stirring bar, rubber septum, and nitrogen inlet, is flushed with dry nitrogen and charged with activated powdered 4 Å molecular sieves (500 mg) and anhydrous DMF (8.3 mL). Under a nitrogen purge, cesium hydroxide monohydrate (280 mg, 1.7 mmol, 1 eq.) is added, and the mixture is vigorously stirred for 10 minutes. After phenethylamine (0.21 mL, 1.7 mmol, 1 eq.) is added, and the mixture is stirred for an additional 30 minutes. By syringe, 2-bromopropane (0.47 mL, 5 mmol, 3 eq.) is added to the white suspension which is stirred at room temperature for an additional 24 hours. The reaction mixture is then filtered to remove the molecular sieves and undissolved inorganic salts, and rinsed several times with ethyl acetate. After the filtrate is concentrated to a nominal volume by blowing air, the residue is taken up in 1 N NaOH, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil.

The resulting crude mixture of products are separated and purified by silica gel column chromatography using a mixture of ethyl acetate-ethanol (9:1 v/v) as the eluting solvent. The common fractions are combined and evaporated to afford dialkylamine K1 (180 mg, 70%) as a colorless oil. The trialkylamine K2 is not observed. Data for K1: $^1$H NMR (360 MHz, CDCl$_3$) δ 1.09 (d, J=8.2 Hz, 6 H), 1.54 (s, NH), 2.62–2.89 (m, 5 H), 7.21–7.31 (m, 5 H). $^{13}$C NMR (90 MHz, CDCl$_3$) δ 22.72, 36.37, 48.49, 48.65, 126.03, 128.58, 139.93.

EXAMPLE 19

Preparation of Dialkylamine Y1

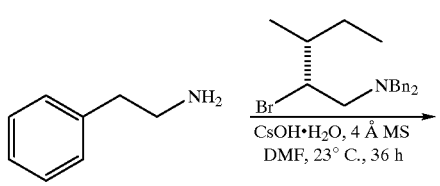

A flame dried 25 mL round-bottomed flask equipped with a magnetic stirring bar, rubber septum, and nitrogen inlet, is flushed with dry nitrogen and charged with activated powdered 4 Å molecular sieves (500 mg) and anhydrous DMF (11 mL). Under a nitrogen purge, cesium hydroxide monohydrate (360 mg, 2.1 mmol, 1 eq.) is added, and the mixture is vigorously stirred for 10 minutes. After phenethylamine (0.26 mL, 2.0 mmol, 1 eq.) is added, the mixture is stirred for an additional 30 minutes. N,N-dibenzylisoleucinol bromide (960 mg, 2.7 mmol, 1.28 eq.) is added to the white suspension which is stirred at room temperature for an additional 36 hours. The reaction mixture is then filtered to remove the molecular sieves and undissolved inorganic salts, and rinsed with ethyl acetate. After the filtrate is concentrated to a nominal volume by blowing air, the residue is taken up in 1 N NaOH, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil.

The resulting crude mixture of products is separated and purified by silica gel column chromatography using a mixture of ethyl acetate-ethanol (9:1 v/v) as the eluting solvent. The common fractions are combined and evaporated to afford dialkylamine Y1 (450 mg, 54%) as a colorless oil. The trialkylamine Y2 is not observed. Data for Y1: $^1$H NMR (360 MHz, CDCl$_3$) δ 0.87–0.92 (m, 6 H), 1.17–1.21 (m, 1 H), 1.43–1.47 (m, 1 H), 1.88 (m, I H), 2.57 (d, J=8.5 Hz, 2 H), 2.66–2.79 (m, 5 H), 2.8 (s, NH), 2.97–3.46 (AB, J$_{AB}$=13.4 Hz, 2 H), 3.74–3.78 (AB, J$_{AB}$=13.7 Hz, 2 H), 7.12–7.41 (m, 15 H). $^{13}$C NMR (90 MHz, CDCl$_3$) δ 12.13, 16.43, 29.07, 32.52, 36.48, 47.31, 51.25, 54.36, 60.95, 126.41, 127.03, 128.42, 128.63, 129.09, 140.25, 140.40.

EXAMPLE 20

Preparation of Dialkylamine W1

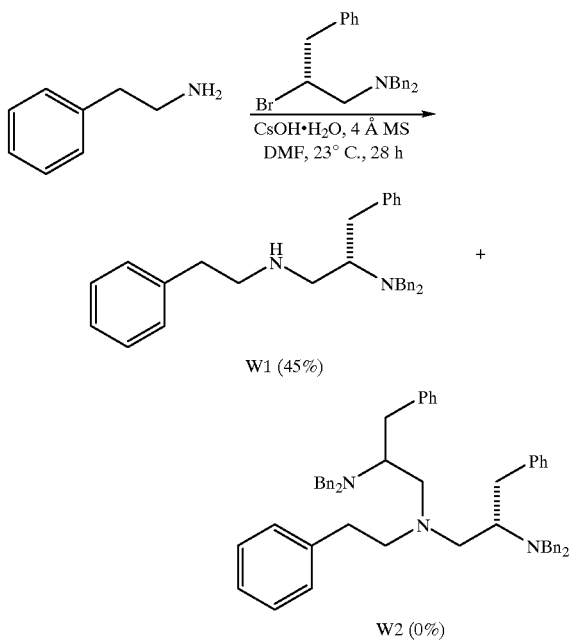

Under an atmosphere of nitrogen, activated 4 Å molecular sieves (500 mg), and cesium hydroxide monohydrate (75 mg, 0.41 mmol, 1 eq.) are added to anhydrous N,N-dimethyl-formamide (2 ml). Phenethylamine (50 mg, 0.61 mmol, 1 eq.) is injected ten minutes later into the turbid solution and stirred for an additional 30 minutes. N,N-dibenzylphenylalaninol bromide (222 mg, 0.55 mmol, 1.5 eq.) is added to the solution and the mixture is allowed to proceed at room temperature under nitrogen for 28 hours. The reaction is then filtered and washed with ethyl acetate. The filtrate is concentrated to a nominal volume by blowing air and the residue is taken up in 1 N NaOH and extracted with ethyl acetate (3×30 mL). The organic layer is washed with water (3×30 mL), followed by brine (30 mL), and then dried using anhydrous sodium sulfate. Solvent is removed in vacuo and the residue is purified via flash column chromatography (9:1 EtOAc:EtOH) to yield the desired dialkylamine W1 (60 mg, 45%) as a clear oil. The trialkylamine W2 was not observed. Data for W1: $^1$H NMR (360 MHz, CDCl$_3$) δ 2.10 (s, NH), 2.34–2.64 (m, 8 H), 2.92–3.10 (m, 1 H), 3.39 (AB, J$_{AB}$=13.4 Hz, 2 H), 3.73 (AB, J$_{AB}$=13.4 Hz, 2 H), 7.05–7.30 (m, 20 H). $^{13}$C NMR (90 MHz, CDCl$_3$) δ 34.23, 38.44, 49.66, 51.29, 53.63, 59.46, 124.35, 125.00, 126.99, 128.38, 128.77, 129.05, 139.50.

EXAMPLE 21

Preparation of Dialkylamine L1

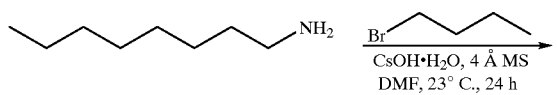

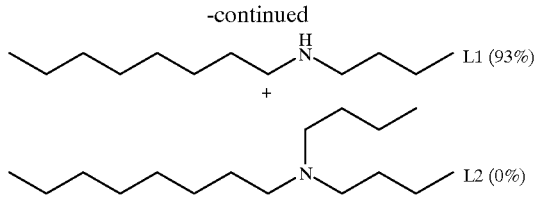

Into a solution of n-octylamine (0.26 mL, 1.57 mmol, 1 eq.) in anhydrous N,N-dimethylformamide (8.0 mL), are added successively activated 4 Å molecular sieves (500 mg) and cesium hydroxide monohydrate (260 mg, 1.56 mmol, 1 eq.). The suspension is stirred under a nitrogen atmosphere for 30 minutes. By syringe, 1-bromobutane (0.20 mL, 2.0 mmol, 1.2 eq.) is added with stirring and the reaction is allowed to proceed under nitrogen for 24 hours at room temperature. The reaction mixture is then filtered to remove molecular sieves and undissolved inorganic salts, followed by washing with ethyl acetate. After the filtrate is concentrated to a nominal volume by blowing air, the residue was taken up in 1 N NaOH solution and extracted with ethyl acetate (3×30 mL). The organic layer was washed with water (2×30 mL), brine (30 mL), and dried over anhydrous sodium sulfate. The solution is concentrated in vacuo, and the residue was purified by flash column chromatography (9:1 EtOAc:EtOH) to give the desired dialkylamine L1 (270 mg, 93%) as a colorless oil. The trialkylamine L2 is not observed. Data for L1: $^1$H NMR (360 MHz, CDCl$_3$) δ 0.86–0.91(m, 6 H), 1.25 (m, 12 H), 1.39 (m, 4 H), 2.35–2.39 (m, 4 H). $^{13}$C NMR (90 MHz, CDCl$_3$) δ 14.06, 20.77, 22.63, 26.96, 27.63, 29.14, 29.29, 29.57, 31.83, 53.90, 54.21.

EXAMPLE 22

Preparation of Dialkylamine M1

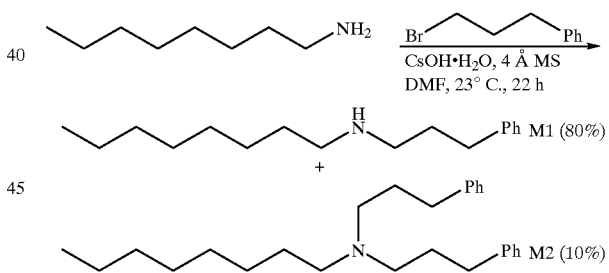

To a solution of n-octylamine (0.26 mL, 1.6 mmol, 1 eq.) in anhydrous N,N-dimethylformamide (8 mL), 4 Å activated molecular sieves (500 mg) and powered cesium hydroxide monohydrate (260 mg, 1.6 mmol, 1 eq.) are added consecutively, and the resulting suspension is stirred vigorously stirred for 30 minutes under a nitrogen atmosphere. Using a syringe, 1-bromo-3-phenylpropane (0.28 mL, 1.9 mmol, 1.2 eq.) is injected into the milky white mixture and the reaction is stirred for 22 hours under an atmosphere of nitrogen at ambient temperature. The reaction mixture is filtered and washed with ethyl acetate. After the filtrate is evaporated to a nominal volume using a gentle stream of air, the residue is taken up in 1 N NaOH and extracted with ethyl acetate (3×30 mL). The resulting organic layer is washed consecutively with water (2×30 mL), brine (30 mL), and dried using anhydrous sodium sulfate. Solvent is removed in vacuo and the residue is subjected to flash column chromatography (9:1 EtOAc:EtOH) to afford the desired dialkylamine M1 (310 mg, 80%) as a colorless oil and the trialkylamine M2 (58 mg, 10%) as a yellow oil. Data for M1: $^1$H NMR (360 MHz, CDCl$_3$) δ 0.85 (t, J=6.8 Hz, 3 H), 1.20–1.35 (m, 8 H), 1.40–1.50 (m, 2 H), 1.78–1.80 (m, 4 H), 3.50–3.70 (m, H), 7.10–7.28 (m, 5 H). $^{13}$C NMR (90 MHz, CDCl$_3$) δ 13.96, 22.52, 27.40, 29.29, 29.39, 29.54, 31.62, 33.56, 40.20, 49.06, 53.61, 126.58, 128.15, 128.31, 141.34. Data for M2: $^1$H NMR (360 MHz, CDCl$_3$) δ 0.90 (t, J=6.9 Hz, 3 H), 1.29 (m, 12 H), 1.90 (t, J=6.4 Hz, 4 H), 2.40–2.49 (m, 6 H), 2.60–2.71 (m, 4 H), 7.16–7.30 (m, 10 H). $^{13}$C NMR (90 MHz, CDCl$_3$) δ 14.04, 22.60, 27.30, 28.10, 29.19, 29.56, 30.11, 31.55, 37.89, 53.61, 54.12, 127.15, 128.33, 128.41, 139.30.

EXAMPLE 23

Preparation of Dialkylamine N1

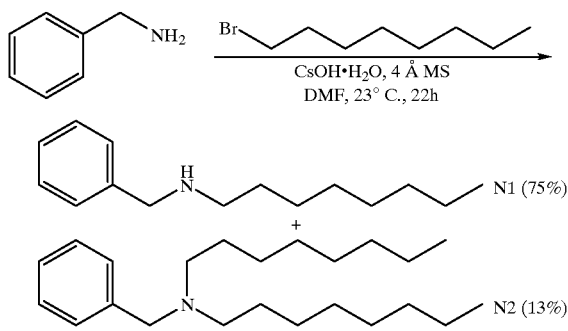

Under an atmosphere of nitrogen, activated 4 Å molecular sieves (500 mg), and cesium hydroxide monohydrate (310 mg, 1.84 mmol, 1 eq.) is added to anhydrous N,N-dimethylformamide (9.4 ml). Benzylamine (0.20 mL, 1.83 mmol, 1 eq.) is injected ten minutes later into the turbid solution and stirred for an additional 30 minutes. 1-Bromooctane (0.39 mL, 2.2 mmol, 1.2 eq.) is added to the solution by syringe and the reaction is allowed to proceed at room temperature under the protection of nitrogen for 22 hours. The reaction is then filtered to remove molecular sieves and undissolved inorganic salts and rinsed with ethyl acetate. After the filtrate is concentrated to a nominal volume by blowing air, the residue is taken up in 1 N NaOH and extracted with ethyl acetate (3×30 mL). The organic layer is washed with water (3×30 mL), followed by brine (30 mL), and then dried using anhydrous sodium sulfate. Solvent is removed in vacuo and the residue is purified via flash column chromatography (9:1 EtOAc:EtOH) to give the desired dialkylamine N1 (300 mg, 75%) as a clear oil and the trialkylamine N2 (75 mg, 13%) as a pale yellow oil. Data for N1: $^1$H NMR (360 MHz, CDCl$_3$) δ 0.88 (t, J=7.0 Hz, 3 H), 1.26–1.31 (m, 10 H), 1.47–1.52 (m, 2 H), 2.25 (s, NH), 2.60 (t, J=7.2 Hz, 2 H), 3.77 (s, 2 H), 7.20–7.33 (m, 5 H). $^{13}$C NMR (90 MHz, CDCl$_3$) δ 14.04, 22.59, 27.25, 29.19, 29.41, 29.56, 31.76, 49.06, 53.61, 127.10, 128.33, 128.40, 139.25. Data for N2: $^1$H NMR (360 MHz, CDCl$_3$) δ 0.86 (t, J=6.8 Hz, 6 H), 1.25–1.31 (m, 20 H), 1.43–1.47 (m, 4 H), 2.38 (t, J=7.2 Hz, 4 H), 3.53 (s, 2 H), 7.21–7.33 (m, 5 H). $^{13}$C NMR (90 MHz, CDCl$_3$) δ 14.07, 22.65, 27.01, 27.42, 29.32, 29.53, 31.86, 53.79, 58.63, 126.49, 127.95, 128.06, 128.29, 128.74, 140.24.

EXAMPLE 24

Preparation of Dialkylamine O1

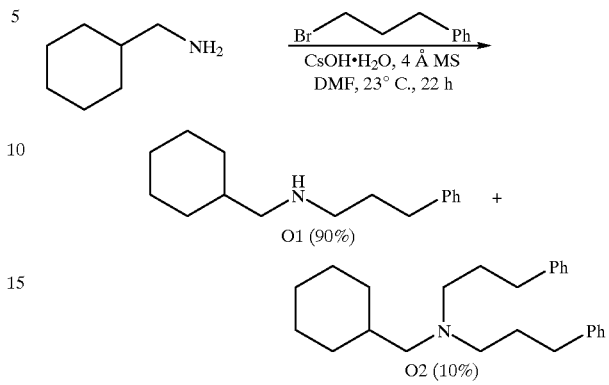

Into a solution of cyclohexylmethyl-amine (0.23 mL, 1.78 mmol, 1 eq.) in anhydrous N,N,-dimethylformamide (9 mL), are added successively activated 4 Å molecular sieves (500 mg) and cesium hydroxide monohydrate (300 mg, 1.78 mmol, 1 eq.), then the suspension is stirred under a nitrogen atmosphere for 30 minutes. By syringe, 1-bromo-3-phenylpropane (0.33 mL, 2.1 mmol, 1.2 eq.) is added with stirring, and the reaction is allowed to proceed under nitrogen for 22 hours at room temperature. The reaction mixture is then filtered to remove molecular sieves and undissolved inorganic salts, followed by washing with ethyl acetate. After the filtrate is concentrated to a nominal volume by blowing air, the residue was taken up in I N NaOH and extracted with ethyl acetate (3×30 mL). The organic layer is washed with water (2×30 mL), brine (30 mL), and dried over anhydrous sodium sulfate. The solution is concentrated in vacuo, and the residue is purified by flash column chromatography (9:1 EtOAc:EtOH) to give the desired dialkylamine O1 (370 mg, 90%) as a colorless oil, and the trialkylamine O2 (62 mg, 10%) as a yellow oil. Data for O1: IR (thin film) 3320, 3084, 3062, 3025, 2850, 2807,1495, 1457, 1128, 745 cm$^{-1}$. $^1$H NMR (360 MHz, CDCl$_3$) δ 0.80–0.90 (m, 2 H), 1.18–1.26 (m, 4 H), 1.39–1.51 (m, 1 H), 1.68–1.82 (m, 6 H), 2.40 (d, J=6.8 Hz, 2 H), 2.58–2.65 (m, 4 H), 7.10–7.28 (m, 5 H). $^{13}$C NMR (90 MHz, CDCl$_3$) δ 24.67, 24.82, 29.72, 29.87, 31.68, 36.10, 47.82, 123.84, 126.32, 126.47, 140.32. Data for M2: $^1$H NMR (360 MHz, CDCl$_3$) δ 0.85–0.87 (m, 2 H), 1.23 (m, 4 H), 1.40–1.45 (m, 1 H), 1.73–1.83 (m, 8 H), 2.18 (d, J=3.8 Hz, 2 H), 2.44 (s, 4 H), 2.65 (s, 4 H), 7.18–7.30 (m, 10 H). hu 3C NMR (90 MHz, CDCl$_3$) δ 26.10, 26.80, 28.88, 31.87, 32.79, 33.57, 36.07, 54.10, 61.61, 125.48, 128.26, 128.37, 142.42.

EXAMPLE 25

Preparation of Dialkylamine P1

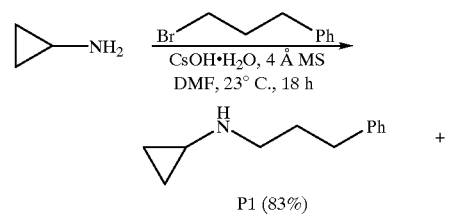

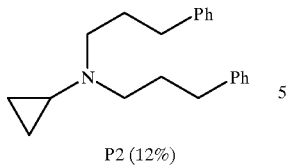

P2 (12%)

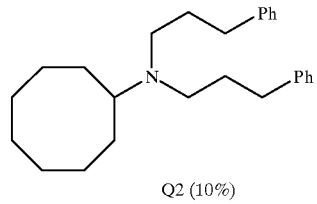

Q2 (10%)

A flame dried 25 mL round-bottomed flask equipped with a magnetic stirring bar, rubber septum, and nitrogen inlet, is flushed with dry nitrogen and charged with activated powdered 4 Å molecular sieves (500 mg) and anhydrous DMF (18 mL). Under a nitrogen purge, cesium hydroxide monohydrate (590 mg, 3.5 mmol, 1 eq.) is added, and the mixture is vigorously stirred for 10 minutes. After cyclopropylamine (0.25 mL, 3.5 mmol, 1 eq.) was added, and the mixture is stirred for an additional 30 minutes. By syringe, 1-bromo-3-phenylpropane (0.7 mL, 4.6 mmol, 1.3 eq.) was added to the white suspension which is stirred at room temperature for an additional 18 hours. The reaction mixture is then filtered to remove the molecular sieves and undissolved inorganic salts, and rinsed several times with ethyl acetate. After the filtrate is concentrated to a nominal volume by blowing air, the residue is taken up in 1 N NaOH, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil.

The resulting crude mixture of products is separated and purified by silica gel column chromatography using a mixture of ethyl acetate-ethanol (9:1 v/v) as the eluting solvent. The common fractions are combined and evaporated to afford dialkylamine P1 (525 mg, 83%) as a colorless oil as well as the trialkylamine P2 (150 mg, 12%) as a pale yellow oil. Data for P1: $^H$ NMR (360 MHz, CDCl$_3$) δ 0.56–0.64 (m, 4 H), 2.03–2.05 (m, 2 H), 2.26–2.31 (m, 1 H), 2.73 (t, J=7.7 Hz, 2 H), 2.88 (t, J=7.2 Hz, 2 H) 4.35 (s, NH), 7.25–7.38 (m, 5 H). $^{13}$C NMR (90 MHz, CDCl$_3$) δ 4.17, 28.11, 30.29, 32.89, 48.37, 126.03, 128.20, 128.35, 140.31. Data for P2: $^1$H NMR (360 MHz, CDCl$_3$) δ 0.56–0.59 (m, 4 H), 1.80–1.86 (m, 1 H), 1.96 (d, J=2.3 Hz, 4 H), 2.70–2.78 (m, 8 H), 7.09–7.53 (m, 10 H). $^{13}$C NMR (90 MHz, CDCl$_3$) δ 6.75, 28.51, 33.83, 36.53, 54.89, 125.55, 128.16, 128.25, 142.37.

EXAMPLE 26

Preparation of Dialkylamine Q1

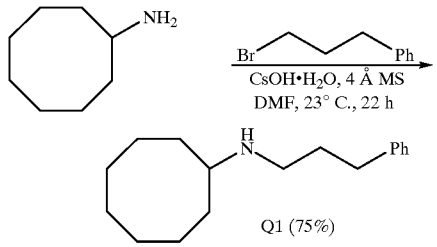

Q1 (75%)

+

Under an atmosphere of nitrogen, activated 4 Å molecular sieves (500 mg), and cesium hydroxide monohydrate (170 mg, 1.65 mmol, 1 eq) is added to anhydrous N,N-dimethylformamide (8 ml). Cyclooctylamine (0.22 mL, 1.65 mmol, 1 eq.) is injected ten minutes later into the turbid solution and stirred for an additional 30 minutes. 1-Bromo-3-phenylpropane (0.29 mL, 1.9 mmol, 1.2 eq.) is added to the solution by syringe and the reaction is allowed to proceed at room temperature under the protection of nitrogen for 22 hours. The reaction is then filtered to remove molecular sieves and undissolved inorganic salts and rinsed with ethyl acetate. The filtrate is concentrated to a nominal volume by blowing air, and the residue is taken up in 1 N NaOH and extracted with ethyl acetate (3×30 mL). The organic layer is washed with water (3×30 mL), followed by brine (30 mL), and then dried using anhydrous sodium sulfate. Solvent is removed in vacuo and the residue is purified via flash column chromatography (9:1 EtOAc:EtOH) to yield the desired dialkylamine Q1 (300 mg, 75%) as a clear oil and the trialkylamine Q2 (58 mg, 10%) as a pale yellow oil. Data for Q1: $^1$H NMR (360 MHz, CDCl$_3$) δ 1.27–1.86 (m, 17 H), 2.61–2.65 (m, 5 H), 7.17–7.39 (m, 5 H). $^{13}$C NMR (90 MHz, CDCl$_3$) δ 24.00, 25.61 27.10, 31.78, 32.52, 33.63, 46.86, 57.78, 125.55, 128.12, 128.17, 141.96. Data for Q2: $^1$H NMR (360 MHz, CDCl$_3$) δ 1.26–1.89 (m, 22 H), 2.54–2.64 (m, 5 H), 7.21–7.33 (m, 10 H). $^{13}$C NMR (90 MHz, CDCl$_3$) δ 23.95, 25.57, 27.06, 31.73, 32.48, 33.59, 46.81, 57.74, 125.50, 128.07, 128.13, 141.92.

EXAMPLE 27

Preparation of Dialkylamine R1

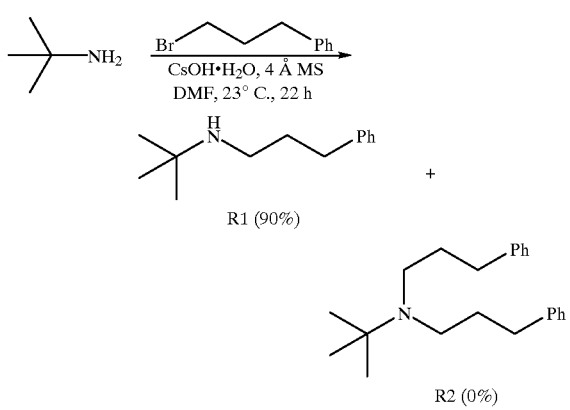

R1 (90%)

+

R2 (0%)

To a flame dried 25 mL round-bottomed flask equipped with a magnetic stirring bar, rubber septum, and nitrogen inlet, is swept with dry nitrogen. The flask is charged with tert-butylamine (0.29 mL, 2.7 mmol, 1 eq.), anhydrous N,N-dimethylformamide (14 mL), activated 4 Å molecular sieves (500 mg), and cesium hydroxide monohydrate (450 mg, 2.7 mmol, 1 eq.). The resulting mixture is allowed to stir for 30 minutes at room temperature. 1-Bromo-3-phenylpropane (0.5 mL, 3.2 mmol, 1.2 eq.) is added by syringe to the white suspension with vigorous stirring. The reaction was allowed to proceed at ambient temperature for 22 hours. The reaction is then filtered and the undissolved inorganic solids are rinsed with ethyl acetate. The filtrate is concentrated by blowing air, and the residue is dissolved in 1 N NaOH, and extracted with ethyl acetate (3×30 mL). The organic layer is washed with water (2×30 mL), brine (30 mL), and dried over anhydrous sodium sulfate. Concentration of the solvent, and purification using flash column chromatography (9:1 EtOAc:EtOH) affords the desired dialkylamine R1 as a clear oil (450 mg, 90%). The trialkylamine R2 is not observed. Data for R1: IR (thin film) 3300, 3062, 3026, 2933, 2859, 2824, 2815, 1496, 1453, 1232 744 cm$^{-1}$; $^1$H NMR (360 MHz, CDCl$_3$) δ 1.08 (s, 9 H), 1.78–1.83 (m, 2 H), 2.05 (s, NH), 2.56–2.64 (m, 4 H), 7.14–7.25 (m, 5 H). $^{13}$CNMR (90 MHz, CDCl$_3$) δ 28.73, 32.26, 33.63, 41.88, 50.31, 125.53, 128.09, 128.17, 141.92.

EXAMPLE 28

Preparation of Dialkylamine U1

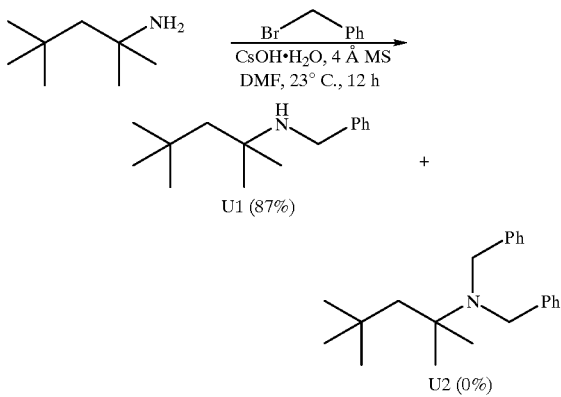

Into a solution of tert-octylamine (0.25 mL, 1.55 mmol, 1 eq.) in anhydrous N,N,-dimethylformamide (8 mL), are added successively activated 4 Å molecular sieves (500 mg) and cesium hydroxide monohydrate (260 mg, 1.55 mmol, 1 eq.). The reaction mixture is stirred under a nitrogen atmosphere for 30 minutes. By syringe, benzyl bromide (0.22 mL, 1.85 mmol, 1.2 eq.) is added and the reaction is allowed to proceed under nitrogen for 12 hours at 23° C. The reaction mixture is then filtered to remove molecular sieves and undissolved inorganic salts, which are washed with ethyl acetate. The filtrate is concentrated to a nominal volume by blowing air and the residue is taken up in 1 N NaOH and extracted with ethyl acetate (3×30 mL). The organic layer is washed with water (2×30 mL), brine (30 mL), and dried over anhydrous sodium sulfate. The solvent is concentrated in vacuo, and the residue is purified by flash column chromatography (9:1 EtOAc:EtOH) to yield the desired dialkylamine U1 (300 mg, 87%) as a colorless oil. The trialkylamine U2 is not observed. Data for U1: $^1$H NMR (360 MHz, CDCl$_3$) δ 1.00 (s, 9 H), 1.17 (s, 6 H), 1.45 (s, 2 H), 3.68 (s, 2 H), 7.04–7.30 (m, 5 H). $^{13}$C NMR (90 MHz, CDCl$_3$) δ 29.04, 31.72, 46.57, 53.01, 54.44, 126.53, 128.07, 128.24, 141.57.

EXAMPLE 29

Preparation of Dialkylamine T1

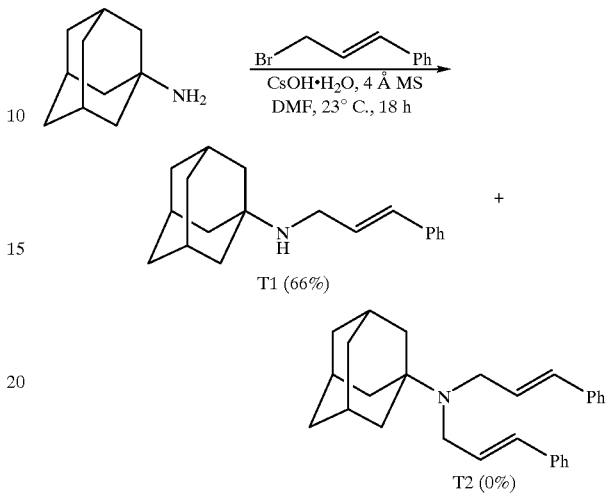

To a solution of 1-adamantylamine (200 mg, 1.32 mmol, 1 eq.) in anhydrous N,N-dimethylformamide (6.6 mL), 4 Å activated molecular sieves (500 mg) and powered cesium hydroxide monohydrate (220 mg, 1.32 mmol, 1 eq.) are added consecutively, and the resulting suspension is vigorously stirred for 30 minutes under a nitrogen atmosphere. Cinnamyl bromide (310 mg, 1.58 mmol, 1.2 eq.) is added into the milky white mixture and the reaction is stirred for 18 hours under an atmosphere of nitrogen at ambient temperature. The reaction mixture is filtered and washed with ethyl acetate. After the filtrate is evaporated to a nominal volume using a gentle stream of air, the residue is taken up in 1 N NaOH and extracted with ethyl acetate (3×30mL). The resulting organic layer is washed consecutively with water (2×30 mL), brine (30 mL), and dried using anhydrous sodium sulfate. Solvent is removed in vacuo and the residue is subjected to flash column chromatography (9:1 EtOAc:EtOH) to afford the desired dialkylamine T1 (230 mg, 66%) as a colorless oil. The trialkylamine TT2 is not observed. Data for TT1: $^1$H NMR (360 MHz, CDCl$_3$) δ 1.58–1.75 (m, 15 H), 2.50 (s, NH), 3.44 (d, J=7.9 Hz, 2 H), 6.35 (dt, J=16.8, 7.4 Hz, 1 H), 6.53 (d, J=16.8 Hz, 1 H), 7.19–7.39 (m, 5 H). $^{13}$C NMR (90 MHz, CDCl$_3$) δ 29.42, 36.47, 42.16, 42.88, 51.46, 126.19, 127.21, 128.38, 131.36, 136.99.

EXAMPLE 30

Preparation of Dialkylamine S1

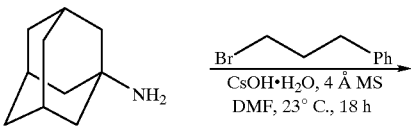

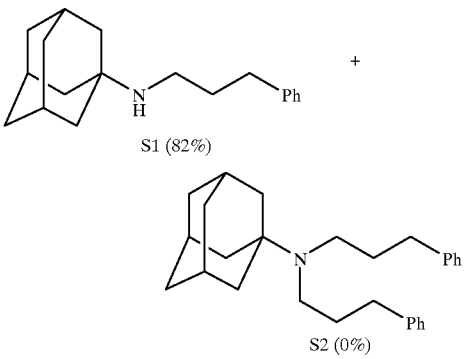

S1 (82%)

S2 (0%)

A flame dried 25 mL round-bottomed flask equipped with a magnetic stirring bar, rubber septum, and nitrogen inlet, is flushed with dry nitrogen and charged with activated powdered 4 Å molecular sieves (500 mg) and anhydrous DMF (8.3 mL). Under a nitrogen purge, cesium hydroxide monohydrate (655 mg, 3.9 mmol, 3 eq.) is added, and the mixture is vigorously stirred for 10 minutes. After 1-adamantylamine (200 mg, 1.3 mmol, 1 eq.) is added, and the mixture is stirred for an additional 30 minutes. By syringe, 1-bromo-3-phenylpropane (0.32 mL, 2.1 mmol, 1.6 eq.) is added to the white suspension which is stirred at room temperature for an additional 18 hours. The reaction mixture is then filtered to remove the molecular sieves and undissolved inorganic salts, and rinsed several times with ethyl acetate. After the filtrate is concentrated to a nominal volume by air, the residue is taken up in 1 N NaOH, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil. The resulting crude mixture of products is separated and purified by silica gel column chromatography using a mixture of ethyl acetate-ethanol (9:1 v/v) as the eluting solvent. The common fractions are combined and evaporated to afford dialkylamine S1 (290 mg, 82%) as a colorless oil. The trialkylamine S2 is not observed. Data for S1: $^1$H NMR (360 MHz, CDCl$_3$) δ 1.57–1.72 (m, 15 H), 1.81–1.90 (m, 2 H), 2.10 (s, NH), 2.62–2.68 (m, 4 H), 7.16–7.30 (m, 5 H). $^{13}$C NMR (90 MHz, CDCl$_3$) δ 29.29, 29.58, 32.14, 33.83, 36.67, 39.86, 41.99, 42.28, 51.48, 125.83, 128.29, 128.44, 141.86.

EXAMPLE 31

Preparation of Dialkylamine X1

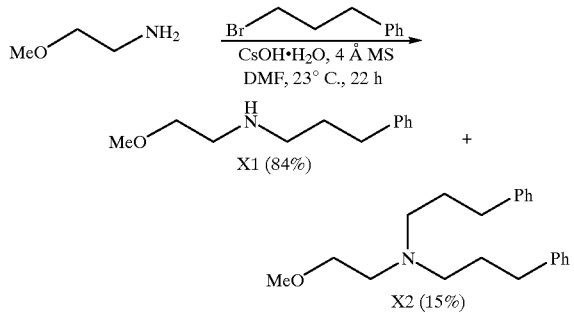

Into a solution of 2-methoxyethylamine (0.23 mL, 2.7 mmol, 1 eq.) in anhydrous N,N-dimethylformamide (13.5 mL), are added successively activated 4 Å molecular sieves (500 mg) and cesium hydroxide monohydrate (450 mg, 2.7 mmol, 1 eq.), then the suspension is stirred under a nitrogen atmosphere for 30 minutes. By syringe, 1-bromo-3-phenylpropane (0.57 mL, 3.7 mmol, 1.4 eq.) is added with stirring, and the reaction is allowed to proceed under nitrogen for 22 hours at room temperature. The reaction mixture is then filtered to remove molecular sieves and undissolved inorganic salts, followed by washing with ethyl acetate. After the filtrate is concentrated to a nominal volume by blowing air, the residue is taken up in 1 N NaOH and extracted with ethyl acetate (3×30 mL). The organic layer is washed with water (2×30 mL), brine (30 mL), and dried over anhydrous sodium sulfate. The solvent is concentrated in vacuo, and the residue is purified by flash column chromatography (9:1 EtOAc:EtOH) to give the desired dialkylamine X1 as a colorless oil (440 mg, 84%), and the trialkylamine X2 (130 mg, 15%) as a yellow oil. Data for X1: $^1$H NMR (360 MHz, CDCl$_3$) δ 1.84–1.90 (m, 2 H), 2.63–2.70 (m, 4 H), 2.80 (t, J=5.1 Hz, 2 H), 3.12 (s, NH), 3.34 (s, 3 H), 3.50 (t, J=5.0 Hz, 2 H), 7.12–7.33 (m, 5 H). $^{13}$C NMR (90 MHz, CDCl$_3$) δ 30.93, 33.30, 48.79, 48.99, 58.63, 71.17, 125.68, 128.21, 141.66. Data for X2: $^1$H NMR (360 MHz, CDCl$_3$) δ 1.77–1.85 (m, 4 H), 2.53–2.57 (m, 4 H), 2.63–2.70 (m, 6 H), 3.33 (s, 3 H), 3.40 (t, J=6.2 Hz, 2 H), 7.17–7.37 (m, 10 H). $^{13}$C NMR (90 MHz, CDCl$_3$) δ 28.65, 33.57, 53.34, 54.07, 58.67, 71.12, 125.70, 128.17, 128.28, 142.25.

EXAMPLE 32

Preparation of Dialkylaminoester V1

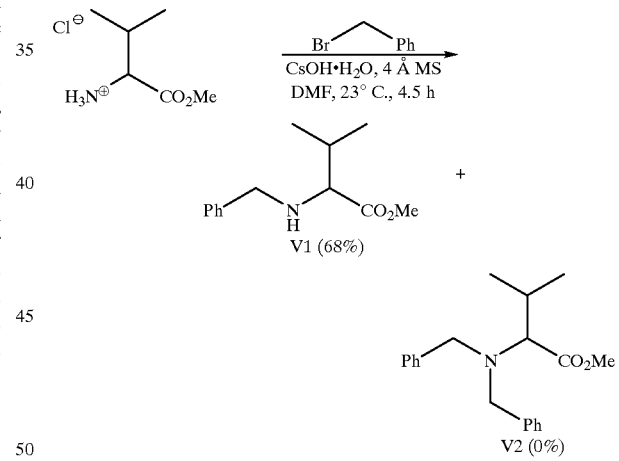

Under an atmosphere of nitrogen, activated 4 Å molecular sieves (500 mg), and cesium hydroxide monohydrate (240 mg, 1.43 mmol, 1.2 eq.) are added to anhydrous N,N-dimethylformamide (12 mL). L-Valine methyl ester hydrochloride (200 mg, 1.2 mmol, 1 eq.) is added ten minutes later into the turbid solution and the mixture is stirred for an additional hour. Benzyl bromide (0.134 mL, 1.2 mmol, 1.3 eq.) is added to the solution by syringe with stirring and the reaction is allowed to proceed at room temperature under nitrogen for 4.5 hours. The reaction is then filtered and washed with ethyl acetate. After the filtrate is concentrated to a nominal volume by blowing air, the residue is purified via flash column chromatography (1:1 hexanes:EtOAc) to yield the desired dialkylaminoester V1 (172 mg, 65%) as a clear oil. The trialkylamine V2 is not observed. Data for V1:

$^1$H NMR (360 MHz, CDCl$_3$) δ 0.94 (d, J=6.8 Hz, 6 H), 1.77 (s, NH), 1.89–1.94 (m, 1 H), 3.01 (d, J=6.1 Hz, 1 H), 3.58 (AB, J$_{AB}$32 12.5 Hz, 1 H), 3.71 (s, 3 H), 3.82 (AB, J$_{AB}$=12.5 Hz, 1 H), 7.23–7.7.32 (m, 5 H). $^{13}$C NMR (90 MHz, CDCl$_3$) δ 18.54, 19.20, 31.59, 51.26, 52.43, 66.44, 126.86, 128.13, 128.16, 139.97, 175.65.

EXAMPLE 33

Preparation of Dialkylaminoester Z1

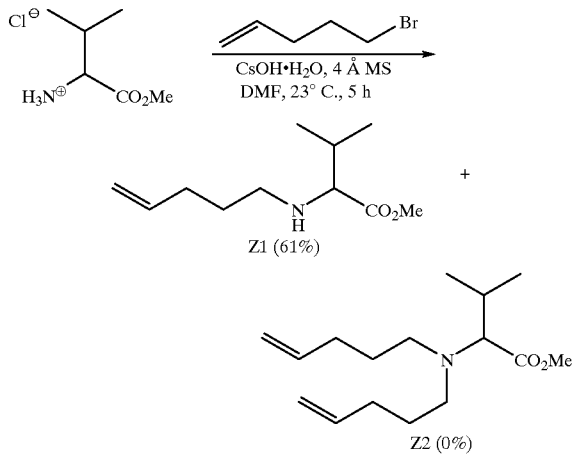

To a solution of L-valine methylester hydrochloride (1 g, 6.0 mmol, 1 eq.) in anhydrous N,N-dimethylformamide (30 mL), 4 Å activated molecular sieves (2.5 g) and powered cesium hydroxide monohydrate (1.1 g, 6.0 mmol, 1.1 eq.) are added consecutively, and the resulting suspension is vigorously stirred for 30 minutes under a nitrogen atmosphere. Using a syringe, 5-bromo-1-pentene (0.85 mL, 7.2 mmol, 1.2 eq.) is injected into the milky white mixture and the reaction is stirred for 10 hours under an atmosphere of nitrogen at ambient temperature. The reaction mixture is then filtered and rinsed with ethyl acetate. After the filtrate is washed with water (3x30 mL), brine (30 mL), and the organic layer is dried over anhydrous sodium sulfate. The solvent is removed in vacuo and the crude product is distilled under reduced pressure to give the dialkylaminoester Z1 as a colorless oil (722 mg, 61%). The trialkylamine Z2 is not observed. Data for Z1: $^1$H NMR (360 MHz, CDCl$_3$) δ 0.95 (d, J=6.8 Hz, 3 H), 0.96 (d, J=6.8 Hz, 3 H), 1.5–1.64 (m, 2 H), 1.62 (s, 1 H), 1.93 (m, 1 H), 2.13 (m, 2 H), 2.41 (m, 1H), 2.61 (m, 1H), 2.95 (d, J=6.1, 1 H), 3.70 (s, 3 H), 4.95 (dd, J=10.2, 1.3 Hz, 1 H), 5.01 (m, 1 H), 5.80 (1H, m). $^{13}$C NMR (90 MHz, CDCl$_3$) δ 18.81. 19.15, 29.33, 31.38, 31.65, 48.12, 51.35, 67.48, 114.30, 138.50, 175.90.

EXAMPLE 34

Preparation of Dialkylaminoester AA1

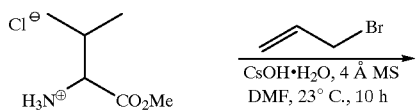

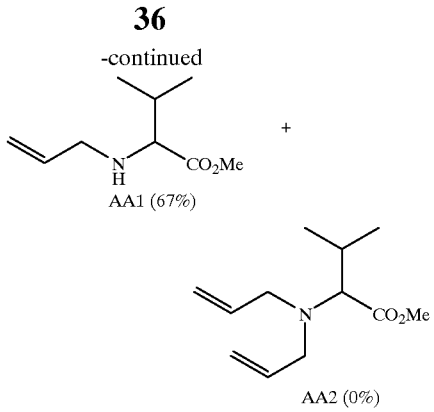

A flame dried 100 mL round-bottomed flask equipped with a magnetic stirring bar, rubber septum, and nitrogen inlet, is flushed with dry nitrogen and charged with activated powdered 4 Å molecular sieves (2.5 g) and anhydrous DMF (30 mL). Under a nitrogen purge, cesium hydroxide monohydrate (1.1 g, 6.6 mmol, 1.1 eq.) is added, and the mixture is vigorously stirred for 10 minutes. After L-valine methyl ester hydrochloride (1 g, 6.0 mmol, 1 eq.) is added, the mixture is stirred for an additional 30 minutes. By syringe, allyl bromide (0.62 mL, 7.2 mmol, 1.2 eq.) is added to the white suspension which is stirred at room temperature for an additional 10 hours. The reaction mixture is then filtered and rinsed with ethyl acetate. After the filtrate is washed with water (3x30 mL), brine (30 mL), and the organic layer is dried over anhydrous sodium sulfate. The solvent is removed in vacuo and the crude product is distilled under reduced pressure to give the dialkylaminoester AA1 as a colorless oil (700 mg, 67%). The trialkylaminoester AA2 is not observed. Data for AA1: $^1$H NMR (360 MHz, CDCl$_3$) δ 0.90 (d, J=6.8 Hz, 3 H), 0.91 (d, J=6.8 Hz, 3 H), 1.55 (m, NH), 1.83 (m, 1 H), 3.02–3.06 (m, 2 H), 3.26 (m, 1 H), 3.65 (s, 3 H), 4.97 (m, 1 H), 5.12 (m, 1 H), 5.80 (ddt, J=17.0, 10.4,6.0Hz, 1 H). $^{13}$C NMR (90 MHz, CDCl$_3$) δ 18.35, 19.21, 31.34, 50.21, 51.03, 66.05, 115.84, 136.31, 156.03, 175.38.

EXAMPLE 35

Preparation of dialkylamino alcohol BB1

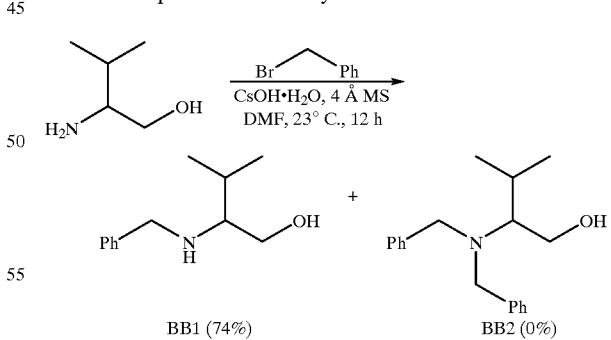

A flame dried 25 mL round-bottomed flask containing a magnetic stirring bar, a rubber septum, is swept with dry nitrogen and charged with L-valinol (0.21 mL, 1.88 mmol, 1 eq.), anhydrous N,N-dimethylformamide (10 ml), activatived 4 Å molecular sieves (500 mg), and cesium hydroxide monohydrate (32 mg, 0.18 mmol, 0.1 eq.). The white suspension is allowed to stir for 30 minutes at room temperature, at which point benzyl bromide (0.27 mL, 2.2 mmol, 1.2 eq.) is added by syringe and the reaction is allowed to proceed at ambient temperature for 12 hours. The reaction is then filtered and the undissolved solids are washed with ethyl acetate. The filtrate is concentrated by air, and direct purification using flash column chromatography (9:1 EtOAc:EtOH) afforded the desired dialkyl amino alcohol BB1 as a clear oil (224 mg, 62%). The trialkylamino alcohol BB2 is not observed. Data for BB1: IR (thin film) 3348, 3104, 3072, 3032, 2960, 2868, 1472, 1038, 709 cm$^{-1}$; $^1$H NMR (360 MHz, CDCl$_3$) δ 0.90 (d, J=6.8 Hz, 3 H), 0.94 (d, J=6.8 Hz, 3 H), 1.84–1.89 (m, 1 H), 2.44–2.45 (m, 3 H), 3.37 (dd, J=17.0 7.2 Hz, 1 H), 3.62 (dd, J=17.0, 7.2 Hz, 1 H), 3.72–3.81 (m, 2 H), 7.09–7.31 (m, 5 H), $^{13}$C NMR (90 MHz, CDCl$_3$) δ 18.39, 19.55, 28.79, 51.32, 60.35, 63.82, 127.10, 128.12, 128.46.

EXAMPLE 36

Preparation of Dimer CC1

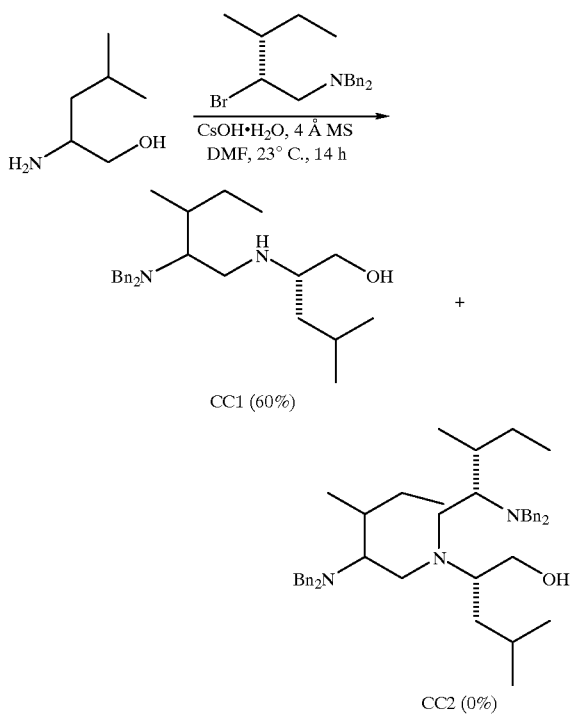

A flame dried 50 mL round-bottomed flask containing a magnetic stirring bar, a rubber septum, is flushed with dry nitrogen and charged with L-leucinol (500 mg, 4.3 mmol, 1 eq.), activatived 4 Å molecular sieves (1 g), and cesium hydroxide monohydrate (717 mg, 4.2 mmol, 1 eq.) are dissolved in anhydrous N,N-dimethylformamide (20 ml) and allowed to stir for 30 minutes at room temperature. N,N-dibenzylisoleucinol bromide (1885 mg, 4.3 mmol, 1.2 eq.) is added to the white suspension with vigorous stirring. The reaction is allowed to proceed at ambient temperature for 14 hours. The reaction is then filtered and the undissolved solids are washed with ethyl acetate. The filtrate is concentrated by air, and the residue is purified using flash column chromatography (5:1 hexanes:EtOAc) which yields the desired dialkylamine CC1 as a clear oil (1005 mg, 60%). The trialkylamine is not observed. Data for CC1: $^1$H NMR (360 MHz, CDCl$_3$) δ 0.86–0.93 (m, 12 H), 1.17–1.19 (m, 2 H), 1.41 (m, 1 H), 1.51–1.54 (m, 2 H), 2.15 (s, 2 H), 2.40–2.47 (m, 2 H), 2.70–2.76 (m, 2 H), 3.30 (m, 1 H), 3.44 (AB, J$_{AB}$=13.5 Hz, 2 H), 3.50–3.53 (m, 1 H), 3.73 (AB, J$_{AB}$=13.5 Hz, 2 H), 7.23–7.37 (m, 10 H). $^{13}$C NMR (90 MHz, CDCl$_3$) δ 11.48, 15.92, 16.32, 26.78, 32.77, 46.00, 54.02, 54.48, 58.32, 59.17, 62.84, 127.09, 128.14, 128.95, 139.7.

EXAMPLE 37

Preparation of Dialkylamine MM1

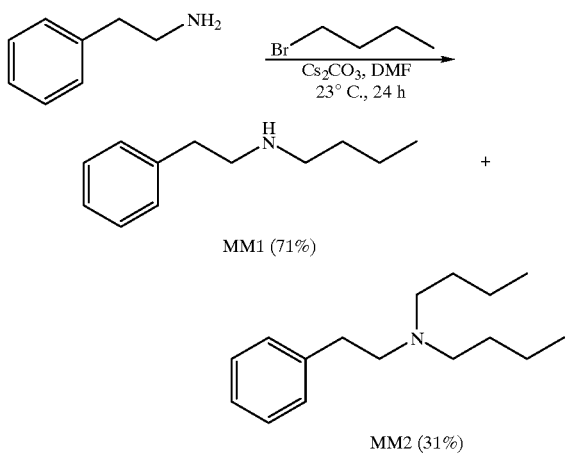

Phenethylamine (0.21 mL, 1.65 mmol, 1 eq.) is dissolved in anhydrous N,N-dimethylformamide (8.3 mL) and powered cesium carbonate (1.610 mg, 6 mmol, 3 eq.), are added consecutively and vigorously stirred for 30 minutes under the protection of nitrogen. Using a syringe, 1-bromobutane (0.21 mL, 2.0 mmol, 1.2 eq.) is injected into the milky white mixture and the reaction is stirred for 23.5 hours under nitrogen at ambient temperature. The reaction mixture is quenched with aqueous 1 N NaOH to dissolve inorganic salts, and extracted with ethyl acetate (3×30 mL). The resulting organic layer is washed consecutively with water (2×30 mL), brine (30 mL), and dried using anhydrous sodium sulfate. Solvent is removed in vacuo and the residue is subjected to flash column chromatography (9:1 EtOAc:EtOH) to afford the desired dialkylamine MM1 (208 mg, 71%) as a colorless oil and the trialkylamine MM2 (120 mg, 31%) as a yellow oil.

EXAMPLE 38

Preparation of Dialkylamine OO1

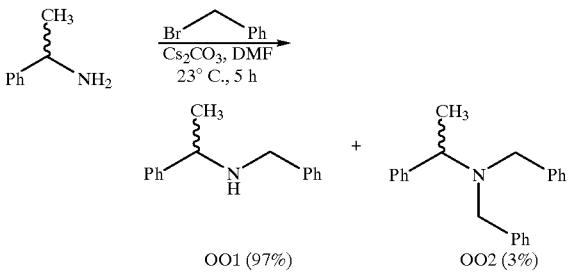

Into a solution of DL-methyl benzyl amine (200 mg, 1.65 mmol, 1 eq.) in anhydrous N,N-dimethylformamide (8.3 mL) is added powdered cesium carbonate (540 mg, 1.65 mmol, 1 eq.), and stirred under a nitrogen atmosphere for 30 minutes. Dropwise, benzyl bromide (0.24 mL, 2.0 mmol, 1.2 eq.) is added with efficient stirring and the reaction is allowed to proceed under the protection of nitrogen for 5 hours at room temperature. The reaction mixture is then filtered to remove undissolved inorganic salts and continually washed with ethyl acetate. The filtrate is concentrated to a nominal volume by blowing air and the residue is taken up in 1 N NaOH and extracted with ethyl acetate (3×30 mL). The organic layer is washed with water (2×30 mL), brine (30 mL), and dried over anhydrous sodium sulfate. The solvent is concentrated in vacuo, and the residue is purified by flash column chromatography (9:1 EtOAc/EtOH) to afford the desired dialkylamine OO1 (340 mg, 97%) as an oil, and the trialkylamine OO2 (15 mg, 3%). Data for OO1: $^1$H NMR (360 MHz, CDCl$_3$) δ 1.33 (d, J=6.5 Hz, 3 H), 1.71 (s, NH), 3.55 (AB J$_{AB}$=14.4 Hz, 1 H), 3.62 (AB, J$_{AB}$=14.4 Hz, 1H), 3.77 (q, J=6.5 Hz, 1 Hz, 1 H), 7.15–7.32 (m, 10 H). $^{13}$C NMR (90 MHz, CDCl$_3$) δ 24.40, 51.86, 57.41, 126.62, 126.77, 126.86, 128.06, 128.28, 128.39. Data for OO2: $^1$H NMR (360 MHz, CDCl$_3$) δ 1.34 (d, J=6.8 Hz, 3 H), 3.37 (AB,J$_{AB}$=13.8 Hz, 2 H), 3.52 (AB,J$_{AB}$=13.8 Hz, 2 H), 3.80–3.86 (q, J=6.8 Hz, 1 H) 7.01–7.31 (m, 15 H). $^{13}$C NMR (90 MHz, CDCl$_3$) δ 13.73, 53.54, 56.13, 126.70, 127.93, 128.00, 128.16, 128.62, 140.42, 142.71.

EXAMPLE 39

Preparation of Dialkylaminoester EE1

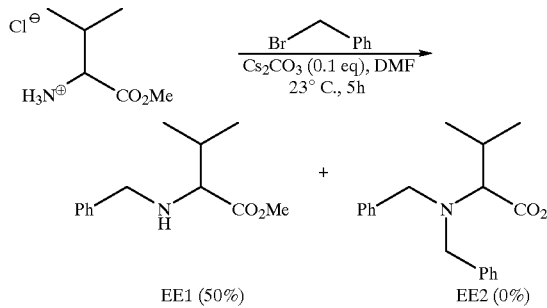

EE1 (50%)  EE2 (0%)

A flame dried 25 mL round-bottomed flask equipped with a magnetic stirring bar, rubber septum, and nitrogen inlet, is flushed with dry nitrogen and charged with anhydrous DMF (8.3 mL). Under a nitrogen purge, powdered cesium carbonate (39 mg, 0.12 mmol, 0.1 eq.) is added, and the mixture is vigorously stirred for 10 minutes. After L-valine methyl ester (200 mg, 1.2 mmol, 1 eq.) is added, and the mixture is stirred for an additional 1 hour. By syringe, benzyl bromide (0.17 mL, 1.44 mmol, 1.2 eq.) is added to the white suspension and stirred at room temperature for 4 hours under nitrogen. The reaction mixture is then filtered to remove the molecular sieves and undissolved inorganic salts, and washed several times with ethyl acetate. After the filtrate is concentrated to a nominal volume by blowing air, the residue is directly purified by silica gel column chromatography using a mixture of hexanes:ethyl acetate(5:1 v/v) as the eluting solvent. The common fractions are combined and evaporated to afford dialkylamino ester EE1 (130 mg, 50%) as a colorless oil. The trialkylamine EE2 is not observed.

EXAMPLE 40

Preparation of Dialkylaminoester FF1

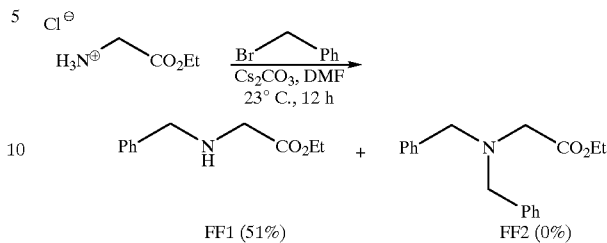

FF1 (51%)  FF2 (0%)

Glycine ethyl ester hydrochloride (200 mg, 1.4 mmol, 1 eq.) is dissolved in anhydrous N,N-dimethylformamide (8 mL, 0.2 M), and powered cesium carbonate (910 mg, 2.8 mmol, 2 eq.) are added consecutively and vigorously stirred for 30 minutes under a nitrogen atmosphere. Using a syringe, benzyl bromide (0.18 mL, 1.54 mmol, 1.1 eq.) is injected into the milky white mixture and the reaction is stirred for 12 hours at ambient temperature. The reaction mixture is filtered and rinsed with ethyl acetate. The filtrate is concentrated to a nominal volume using a gentle stream of air, and the residue is subjected to flash column chromatography (1:1 hexanes:EtOAc) to afford the desired dialkylaminoester FF1 (138 mg, 51%) as a colorless oil. The trialkylamine FF2 is not observed. Data for FF1 $^1$H NMR (360 MHz, CDCl$_3$) δ 1.20 (t, J=12.0 Hz, 3 H), 1.90 (s, NH), 3.28 (s, 2 H), 3.75 (s, 2 H), 4.09 (q, J=9.6 Hz, 2 H), 7.15–7.35 (m, 5 H.

EXAMPLE 41

Preparation of Dialkylaminoester HH1

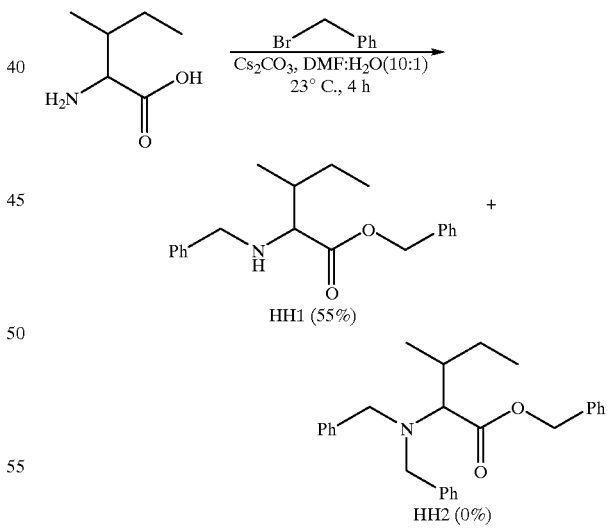

HH1 (55%)

HH2 (0%)

A flame dried 25 mL round-bottomed flask equipped with a magnetic stirring bar, rubber septum, and nitrogen inlet, is flushed with dry nitrogen and charged with anhydrous DMF (8 mL) and distilled water (0.8 mL) (10:1 v/v). Under a nitrogen purge, powered cesium carbonate (487 mg, 1.5 mmol, 1 eq.) is added, and the mixture is vigorously stirred for 10 minutes. After L-isoleucine (196 mg, 1.5 mmol, 1 eq.) is added, and the mixture is stirred for 30 minutes. By syringe, benzyl bromide (0.36 mL, 3.0 mmol, 2 eq.) is added to the white suspension, which is stirred at room temperature for an additional 3.5 hours. The reaction mixture is then filtered to remove the undissolved inorganic salts, and washed several times with ethyl acetate. After the filtrate is concentrated to a nominal volume by blowing air, the residue is purified by silica gel column chromatography using a mixture of hexanes:ethyl acetate (5:1 v/v) as the eluting solvent. The common fractions are combined and evaporated to afford dialkylaminoester HH1 (256 mg, 55%) as a colorless oil. The trialkylaminoester HH2 is not observed. $^{11}$H NMR (360 MHz, CDCl$_3$) δ 0.81–0.96 (m, 6 H), 1.23–1.29 (m, 1 H), 1.60–1.64 (m, 1 H), 1.64–1.78 (m, 1 H), 1.88 (s, NH), 3.20 (d, J=6.2 Hz, 1 H), 3.64 (AB, J$_{AB}$=12.9 Hz, 1 H), 3.87 (AB, J$_{AB}$=12.9 Hz, 1 H), 5.22 (s, 2 H), 7.25–7.43 (m, 10 H).

EXAMPLE 42

Preparation of Dialkylamine I11

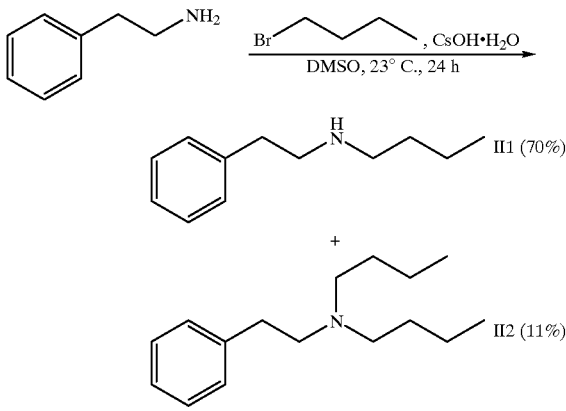

A flame dried 25 mL round-bottomed flask equipped with a magnetic stirring bar, rubber septum, and nitrogen inlet, is flushed with dry nitrogen and anhydrous DMSO (8.3 mL) is added. Under a nitrogen purge, cesium hydroxide monohydrate (285 mg, 1.7 mmol, 1 eq.) is added, and the mixture is vigorously stirred for 10 minutes. After phenethylamine (0.21 mL, 1.7 mmol, 1 eq.) is added, the mixture is stirred for an additional 30 minutes. By syringe, 1-bromobutane (0.21 mL, 2.0 mmol, 1.2 eq.) is added to the white suspension which is stirred at room temperature for an additional 23.5 hours. The reaction mixture is then filtered to remove the molecular sieves and undissolved inorganic salts, and rinsed several times with ethyl acetate. After the filtrate is concentrated to a nominal volume by blowing air, the residue is taken up in 1 N NaOH, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil. The resulting crude mixture of products is separated and purified by silica gel column chromatography using a mixture of ethyl acetate-ethanol (9:1 v/v) as the eluting solvent. The common fractions are combined and evaporated to afford dialkylamine I11 II(209 mg, 70%) as a colorless oil as well as trialkylamine 2 (43 mg, 11%) as a pale yellow oil.

EXAMPLE 43

Preparation of Dialkylamine JJ1

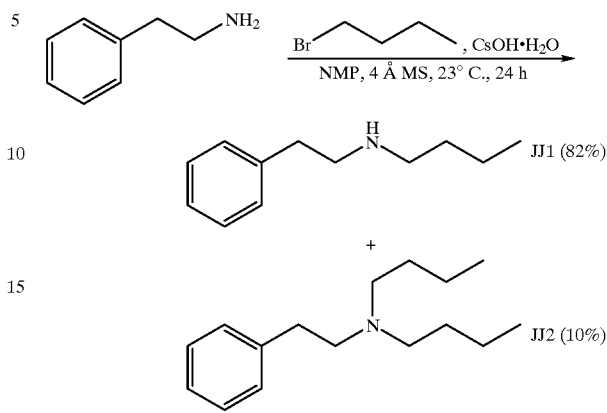

A flame dried 25 mL round-bottomed flask equipped with a magnetic stirring bar, rubber septum, and nitrogen inlet, is flushed with dry nitrogen and charged with phenethylamine (0.21 mL, 1.65 mmol, 1 eq.), anhydrous 1-methyl-2-pyrrolidinone (8.3 mL), activatived 4 Å molecular sieves (500 mg), and cesium hydroxide monohydrate (285 mg, 1.65 mmol, 1 eq.). The white suspension is allowed to stir for 30 minutes at room temperature. 1-Bromobutane (0.2 mL, 2.0 mmol, 1.2 eq.) is added by syringe to the white suspension and the reaction is vigorously stirred at ambient temperature for 23.5 hours under a nitrogen atmosphere. The reaction is then filtered and the undissolved solids are rinsed with ethyl acetate. The filtrate is concentrated by blowing air, and the residue is dissolved in 1 N NaOH, and extracted with ethyl acetate (3×30 mL). The organic layer is washed with water (2×30 mL), brine (30 mL), and dried over anhydrous sodium sulfate. Concentration of the solution, and purification using flash column chromatography (9:1 EtOAc:EtOH) yielded the desired dialkylamine JJ1 as a clear oil (242 mg, 83%) and the trialkylamine JJ2 (38 mg, 10%) as a yellow oil.

EXAMPLE 44

Preparation of Dialkylamine KK1

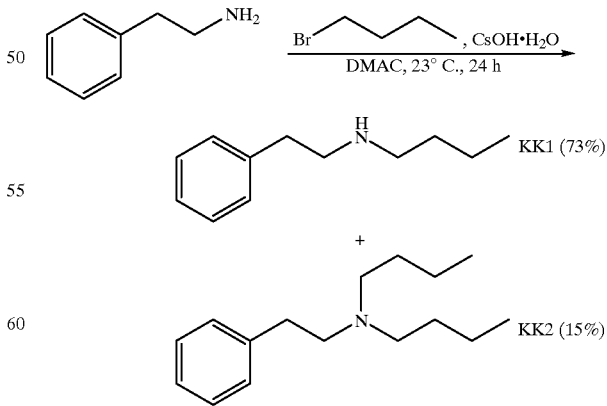

Under an atmosphere of nitrogen, with stirring, activated 4 Å molecular sieves (500 mg), and cesium hydroxide monohydrate (280 mg, 1.65 mmol, 1 eq.) is added to anhydrous N,N-dimethylacetamide (8.3 mL). Phenethylamine (0.21 mL, 1.65 mmol, 1 eq.) is injected ten minutes later into the turbid solution and stirred an additional 30 minutes at room temperature. 1-Bromobutane (0.21 mL, 2.0 mmol, 1.2 eq.) is added to the solution by syringe and the reaction is allowed to proceed at room temperature under nitrogen for 24 hours. The reaction is then filtered to remove undissolved solids and rinsed with ethyl acetate. The filtrate is concentrated by evaporating using air to a nominal volume and the residue is taken up in 1 N NaOH and extracted with ethyl acetate (3×30 mL). The organic layer is washed with water (3×30 mL), followed by brine (30 mL), and then dried over anhydrous sodium sulfate. Solvent is removed in vacuo and the residue is purified via flash column chromatography (9:1 EtOAc:EtOH) to afford the desired dialkylamine KK1 (213 mg, 73%) as a clear oil and the trialkylamine KK2 (60 mg, 15%) as a pale yellow oil.

EXAMPLE 45

Preparation of Dialkylsilylamine DD1

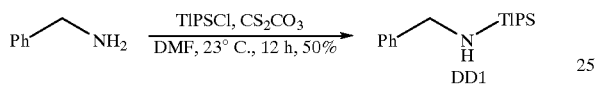

Under an atmosphere of nitrogen, with stirring, powdered cesium carbonate (920 mg, 2.8 mmol, 1.5 eq.) is added to anhydrous N,N-dimethylformamide (9.5 ml). Benzylamine (0.5 mL, 1.86 mmol, 1 eq.) is injected ten minutes later into the turbid solution and stirred for an additional 30 minutes. Triisopropylsilyl chloride (0.40 mL, 2.05 mmol, 1.1 eq.) is added to the solution by syringe with stirring and the reaction is allowed to proceed at room temperature under the protection of nitrogen overnight. The reaction is then filtered to remove undissolved solids and washed with ethyl acetate. The filtrate is washed with water (3×30 mL) and the organic layer is washed with brine (30 mL), and dried using anhydrous sodium sulfate. Solvent is removed in vacuo and the residue is purified via flash column chromatography (5:1 hexanes:EtOAc) to yield the desired silyl protected dialkylamine DD1 (200 mg, 50%) as a clear yellow oil. Data for DD1: $^1$H NMR (360 MHz, CDCl$_3$) δ 0.89–0.90 (m, 21 H), 2.90 (s, NH), 4.25 (s, 2 H), 7.10–7.25 (m, 5 H). $^{13}$C NMR (90 MHz, CDCl$_3$) δ 12.23, 17.61, 41.93, 126.81, 126.97, 127.60, 128.54.

EXAMPLE 46

Preparation of Dialkylamine LL1

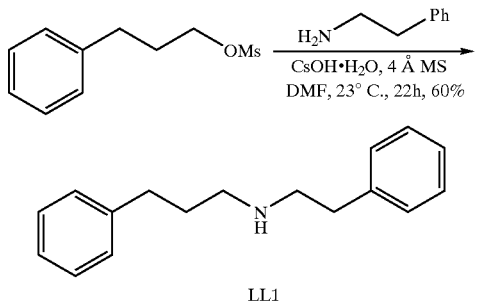

Phenethylamine (0.15 mL, 1.2 mmol, 1 eq.) is dissolved in anhydrous N,N-dimethylformamide (6 mL), 4 Å activated molecular sieves (500 mg) and powered cesium hydroxide monohydrate (200 mg, 1.2 mmol, 1 eq.) are added consecutively and the suspension is vigorously stirred for 30 minutes under nitrogen. Dropwise, a solution of 3-phenyl-1-propyl mesylate (308 mg, 1.5 mmol, 1.44 eq.) is dissolved in DMF and injected into the milky white solution. The reaction is stirred for 21.5 hours under an atmosphere of nitrogen at ambient temperature. The reaction mixture is filtered to remove undissolved sieves and inorganic salts, and rinsed with ethyl acetate. The filtrate is evaporated to a nominal volume using a gentle stream of air, and the residue is taken up in 1 N NaOH and extracted with ethyl acetate (3×30 mL). The resulting organic layer is washed consecutively with water (2×30 mL), brine (30 mL), and dried using anhydrous sodium sulfate. Solvent is removed in vacuo and the residue is subjected to flash column chromatography (9:1 EtOAc:EtOH) to afford the desired dialkylamine LL1 (173 mg, 60%) as a colorless oil.

EXAMPLE 47

Preparation of Dialkylamine LL1'

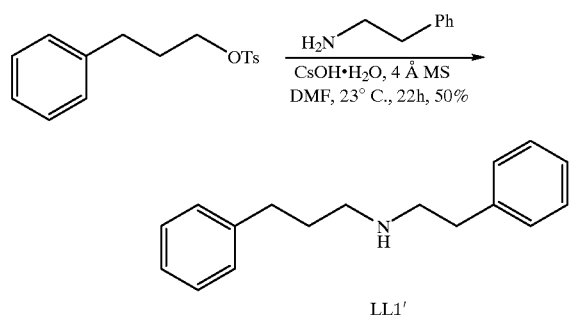

Into a solution of phenethylamine (75 mg, 0.62 mmol, 1 eq.) in anhydrous N,N-dimethylformamide (4 mL) are added successively activated 4 Å molecular sieves (500 mg), and cesium hydroxide monohydrate (100 mg, 0.62 mmol, 1 eq.), and the turbid white mixture is stirred for 30 minutes. Dropwise, a solution of 3-phenyl-1-propyl tosylate in DMF (220 mg, 0.75 mmol, 1.2 eq.) formed by a known literature procedure, is added with stirring and the reaction is allowed to proceed under nitrogen for 21.5 hours at 23° C. The reaction mixture is then filtered to remove molecular sieves and undissolved inorganic salts and continually rinsed with ethyl acetate. The filtrate is concentrated to a nominal volume by blowing air and the residue is taken up in 1 N NaOH and extracted with ethyl acetate (3×30 mL). The organic layer is washed with water (2×30 mL), brine (30 mL), and dried over anhydrous sodium sulfate. The solvent was concentrated in vacuo and the residue was purified by flash column chromatography (9:1 EtOAc:EtOH) to afford the desired dialkylamine LL1' (74 mg, 50%) as a colorless oil.

EXAMPLE 48

One Pot Preparation of Dialkylamine LL1"

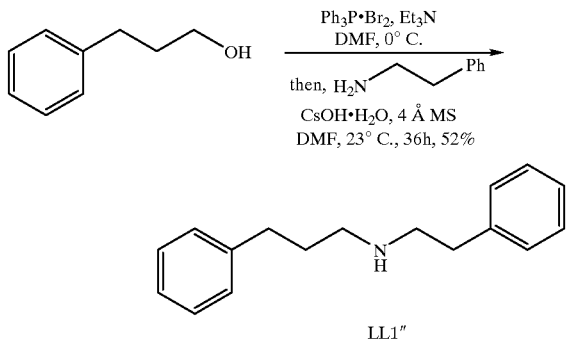

LL1"

Into a solution of 3-phenyl-1-propanol (0.2 mL, 1.46 mmol, 1 eq.) in anhydrous N,N-dimethylformamide (8 mL) are added successively dry triethylamine (0.31 mL, 2.2 mmol, 1.5 eq.), and triphenylphosphine dibromide (800 mg, 2 mmol, 1.3 eq.). The reaction mixture is then stirred under a nitrogen atmosphere for 1 hour at 0° C. Upon consumption of the starting material (alcohol), by syringe, phenethylamine (0.15 mL, 2.0 mmol, 1.2 eq.) and cesium hydroxide monohydrate (200 mg, 1.65 mmol, 1.2 eq.) are added with stirring and the reaction is allowed to proceed for 36 hours. The reaction mixture is then filtered to remove molecular sieves and undissolved inorganic salts and continually rinsed with ethyl acetate. The filtrate is concentrated to a nominal volume by blowing air and the residue is taken up in I N NaOH, and extracted with ethyl acetate (3×30 mL). The organic layer is washed with water (2×30 mL), brine (30 mL), and dried over anhydrous sodium sulfate. The solvent is concentrated in vacuo, and the residue is purified by flash column chromatography (9:1 EtOAc:EtOH) to give (140 mg, 52%) of the desired dialkylamine LL1" as a clear oil.

EXAMPLE 49

One Pot Preparation of Dialkylamine LL1'''.

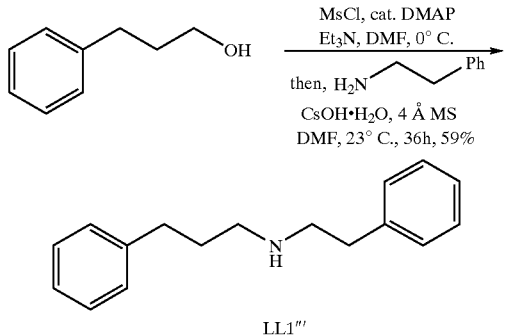

LL1'''

Into a solution of 3-phenyl-1-propanol (0.21 mL, 1.55 mmol, 1 eq.) in anhydrous N,N-dimethylformamide (8 mL) are added successively dry triethylamine (0.26 mL, 1.86 mmol, 1.2 eq.), catalytic amount of dimethylaminopyridine (DMAP), followed by methanesulfonyl chloride (0.143 mL, 1.86 mmol, 1.2 eq.) and the reaction is stirred under a nitrogen atmosphere for 1 hour at 0° C. Upon consumption of the starting material (alcohol), by syringe, phenethylamine (0.15 mL, 1.2 mmol, 1.0 eq.) and cesium hydroxide monohydrate (200 mg, 1.2 mmol, I eq.) is added with stirring and the reaction is allowed to proceed for 36 hours at room temperature. The reaction mixture is then filtered to remove molecular sieves and undissolved inorganic salts and continually washed with ethyl acetate. The filtrate is concentrated to a nominal volume by blowing air and the residue is taken up in 1 N NaOH and extracted with ethyl acetate (3×30 mL). The organic layer is washed with water (2×30 mL), brine (30 mL), and dried over anhydrous sodium sulfate. The solvent is concentrated in vacuo, and the residue is purified by flash column chromatography (9:1 EtOAc:EtOH) to give the desired dialkylamine LL1'''. (170 mg, 59%) as a clear oil.

EXAMPLE 50

One-Pot Preparation of Dialkylamine NN1

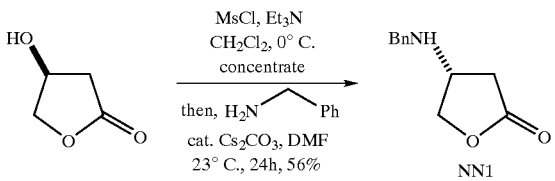

A flame dried 25 mL round-bottomed flask equipped with a magnetic stirring bar, rubber septum, and nitrogen inlet, is flushed with dry nitrogen and charged with δ-butyrolactone (0.16 mL, 1.94 mmol, 1 eq.), and dry methylene chloride (10 mL). The reaction mixture is cooled to 0° C. and dry triethylamine (0.33 mL, 2.2 mmol, 1.2 eq.), methanesulfonyl chloride (0.17 mL, 2.2 mmol, 1.2 eq.) are added and the reaction is allowed to warm to room temperature and allowed to stir for two hours. The crude reaction mixture is evaporated and taken up in N,N-dimethylformamide (10 mL) and benzylamine (0.21 mL, 1.94 mmol, 1 eq.) is added, followed by a catalytic amount of powered cesium carbonate (50 mg). The reaction is stirred at room temperature for 24 hours under the protection of a nitrogen atmosphere. The reaction is quenched with water to dissolve inorganic salts, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil. The resulting crude mixture purified by silica gel column chromatography using a mixture of hexanes:ethyl acetate (1:1 v/v) as the eluting solvent. The common fractions are combined and evaporated to afford dialkylamine NN1 (246 mg, 56%) as an oil. Data for NN1: $^1$H NMR (360 MHz, CDCl$_3$) δ 1.77 (s, NH), 2.20 (dd, J=7.2, 3.4 Hz, 1 H), 2.50 (dd, J=7.5, 4.5 Hz, 1 H), 3.50–3.55 (m, 1 H), 3.65 (m, 2 H), 3.94 (dd, J=7.5, 3.7 Hz, 1 H), 4.21 (dd, J=7.5, 5.7 Hz, 1 H), 7.15–7.21 (m, 5 H). $^{13}$C NMR (90 MHz, CDCl$_3$) δ 35.37, 51.32, 53.46, 73.10, 127.46, 127.69, 128.52, 139.09, 176.09.

EXAMPLE 51

One-Pot Preparation of Dialkylamine NN2

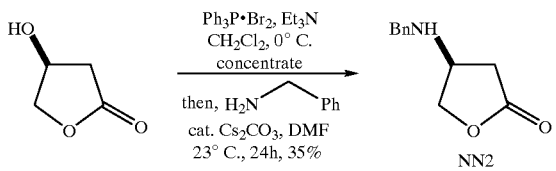

A flame dried 25 mL round-bottomed flask equipped with a magnetic stirring bar, rubber septum, and nitrogen inlet, is flushed with dry nitrogen and charged with δ-butyrolactone (0.16 mL, 1.96 mmol, 1 eq.), and dry methylene chloride (10 mL). The reaction mixture is cooled to 0° C. and triphenylphosphine dibromide (1082 mg, 2.54 mmol, 1.3 eq.) is added and the reaction is allowed to warm to room temperature and allowed to stir for two hours. Upon completion of the starting material (alcohol), the crude reaction mixture is evaporated and taken up in N,N-dimethylformamide (10 mL) and benzylamine (0.2 mL, 1.96 mmol, 1 eq.) is added followed by a catalytic amount of powered cesium carbonate (50 mg). The reaction is then stirred at room temperature for 24 hours under the protection of nitrogen. The reaction is quenched with water to dissolve inorganic salts, and transferred to a 125 mL separatory funnel. The basic aqueous phase is extracted with ethyl acetate (4×20 mL), and the combined organic layers are washed with brine, dried over anhydrous sodium sulfate, filtered, and concentrated in vacuo to give a pale yellow oil. The resulting crude mixture purified by silica gel column chromatography using a mixture of ethyl acetate-ethanol (9:1 v/v) as the eluting solvent. The common fractions are combined and evaporated to afford dialkylamine NN2 (156 mg, 35%) as an oil.

EXAMPLE 52

Synthesis of 1,8-Diamino-3-thia-6-azaoctane from 2-Thioethylamine Hydrochloride

In a 500 mL round bottom flask, are placed 2-thioethylamine hydrochloride (2.0 g, 18 mmol), DMF (90 mL), 4 Å molecular sieves (10 g), cesium hydroxide monohydrate (21 g, 130 mmol), and 2-bromoethylamine hydrobromide (11 g, 54 mmol). The reaction mixture is mechanically stirred at room temperature for 44 h at which time the reaction is quenched with 200 mL of 1 M NaOH. Following filtration, the solution is evaporated by blowing on the surface with a stream of air. The resulting solid is then taken up in a small amount of methanol, triturated with $Et_2O$, subsequently filtered, and reduced to dryness in vacuo. Trituration is repeated two more times to ensure the removal of the inorganic salts. The resulting thick yellow oil is then subjected to silica gel chromatography using a mobile phase of 5% $NH_4OH$ in MeOH, followed by 15% $NH_4OH$ in MeOH. Following concentration of the appropriate fractions, 0.96 g (44% yield) of intermediate 1,5-diamino-3-thiapentan and 0.716 g (24% yield) of 1,8-diamino-3-thia-6-azaoctane is obtained.

EXAMPLE 53

Synthesis of 1,8-Diamino-3-thia-6-azaoctane from 1,5-Diamino-3-Thiapentane

In a 250 mL round bottom flask, are placed 1,5-diamino-3-thiapentane (1.1 g, 8.8 mmol), DMF (45 mL), 4 Å molecular sieves (5.0 g), cesium hydroxide monohydrate (3.7 g, 22 mmol), and 2-bromo-ethylamine hydrobromide (2.7 g, 13 mmol). The reaction mixture is mechanically stirred at room temperature for 12 h at which time the reaction is quenched with 100 mL of 1 M NaOH. Following filtration, the solution is evaporated by blowing on the surface with a stream of air. The resulting solid is then taken up in a small amount of methanol, triturated with $Et_2O$, subsequently filtered, and reduced to dryness in vacuo. Trituration is repeated two more times to ensure the removal of the inorganic salts. The resulting thick yellow oil is then subjected to silica gel chromatography using a mobile phase of 5% $NH_4OH$ in MeOH, followed by 15% $NH_4OH$ in MeOH. Collection of the fractions containing 1,8-diamino-3-thia-6-azaoctane resulted in 1.04 g (73% yield) of pure material.

EXAMPLE 54

Preparation of Dimer RR2

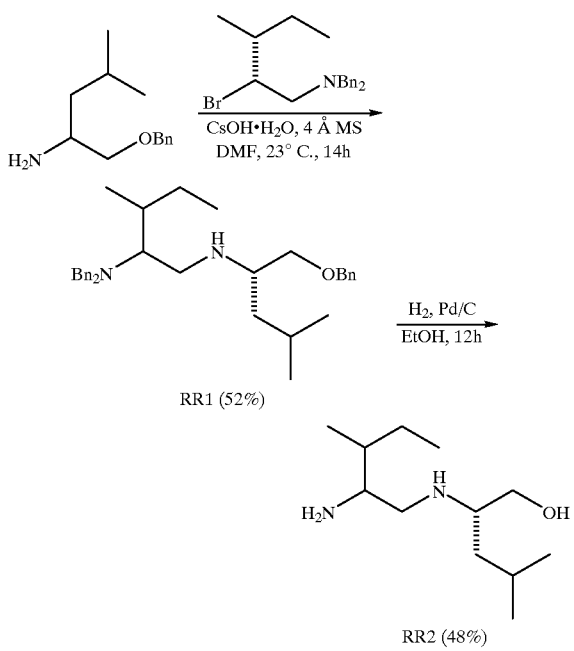

A flame dried 25 mL round-bottomed flask containing a magnetic stirring bar, a rubber septum, is flushed with dry nitrogen and charged with L-leucine benzyl ether (88 mg, 0.4 mmol, 1 eq.), prepared by a known literature procedure, activatived 4 Å molecular sieves (100 mg), and cesium hydroxide monohydrate (70 mg, 0.4 mmol, 1 eq.) are dissolved in anhydrous N,N-dimethylformamide (2 ml) and allowed to stir for 30 minutes at room temperature. N,N-dibenzylisoleucinol bromide (220 mg, 0.6 mmol, 1.5 eq.) is added to the white suspension with vigorous stirring. The reaction is allowed to proceed at ambient temperature for 14 hours. The reaction is then filtered and the undissolved solids are washed with ethyl acetate. The filtrate is concentrated by air, and the residue is purified using flash column chromatography (1:1 hexanes:EtOAc) which yielded the desired protected dimer RRI as an oil (100 mg, 52%). The trialkylamine is not observed. Protected dimer RR1 is then hydrogenated to give dimer RR2 (22 mg, 48 % yield). Data for RR1: $^1$H NMR (360 MHz, $CDCl_3$) δ 0.85–0.93 (m, 12 H), 1.15–1.20 (m, 2 H), 1.41 (m, 1 H), 1.51–1.54 (m, 2 H), 2.15 (s, 2 H), 2.40–2.47 (m, 2 H), 2.7–2.76 (m, 2 H), 3.30 (m, 1 H), 3.44 (AB, $J_{AB}$=13.5 Hz, 2 H), 3.47 (m, 1 H), 3.71 (AB, $J_{AB}$=13.5 Hz, 2 H), 4.59–4.53 (m. 2 H), 7.24–7.33 (m, 15 H).

EXAMPLE 55

Preparation of Dimer SS2

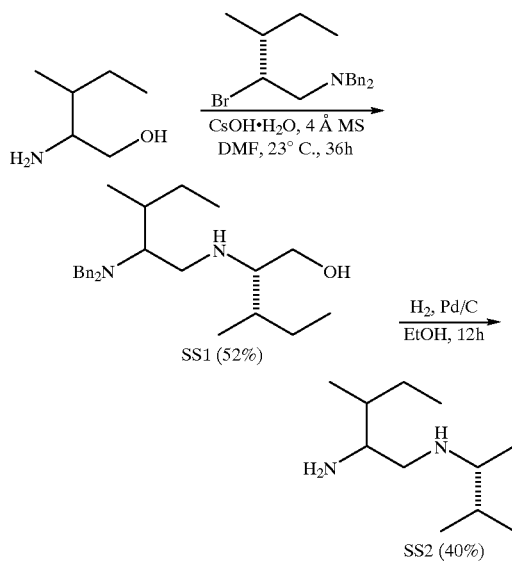

A flame dried 250 mL round-bottomed flask containing a magnetic stirring bar, a rubber septum, is flushed with dry nitrogen and charged with L-Isoleucinol (1730 mg, 14.8 mmol), activatived 4 Å molecular sieves (1000 mg), and cesium hydroxide monohydrate (2500 mg, 14.8 mmol, 1 eq.) are dissolved in anhydrous N,N-dimethylformamide (74 ml) and allowed to stir for 30 minutes at room temperature. N,N-dibenzylisoleucinol bromide (6350 mg, 17.6 mmol, 1.2 eq.) is added to the white suspension with vigorous stirring. The reaction is allowed to proceed at ambient temperature for 36 hours. The reaction is then filtered and the undissolved solids are washed with ethyl acetate. The filtrate is concentrated by air, and the residue is purified using flash column chromatography (1:1 hexanes:EtOAc) which yielded the desired protected dimer SS1 as an oil (3000 mg, 52%). The trialkylamine is not observed. Protected dimer SS1 is then deprotected by hydrogentation to give the dimer SS2 (900 mg, 40% yield). Data for SS1: $^1$H NMR (360 MHz, CDCl$_3$) δ 0.74–0.92 (m, 12 H), 1.09 (m, 1 H), 1.21–1.26 (m, 2 H), 1.60–1.63 (m, 2 H), 1.88 (m, 2 H), 2.19 (s, 2 H), 2.57–2.65 (m, 3 H), 2.88 (m, 1 H), 3.53–3.54 (m, 1 H), 3.60 (AB, J$_{AB}$=13.5 Hz, 2 H), 3.88 (m, 1 H), 3.88 (AB, J$_{AB}$=13.5 Hz, 2 H), 7.25–7.38 (m, 10 H). Data for SS2: $^1$H NMR (360 MHz, CDCl$_3$) δ 0.74–0.86 (m, 12 H), 1.22–1.52 (m, 5 H), 1.73–1.85 (m, 2 H), 2.87–2.93 (m, 2 H), 3.34 (m, 1 H), 3.71–3.73 (m, 1 H), 3.80–3.83 (m, 1 H), 6.88 (br s, 4 H).

EXAMPLE 56

Preparation of Trimer TT1

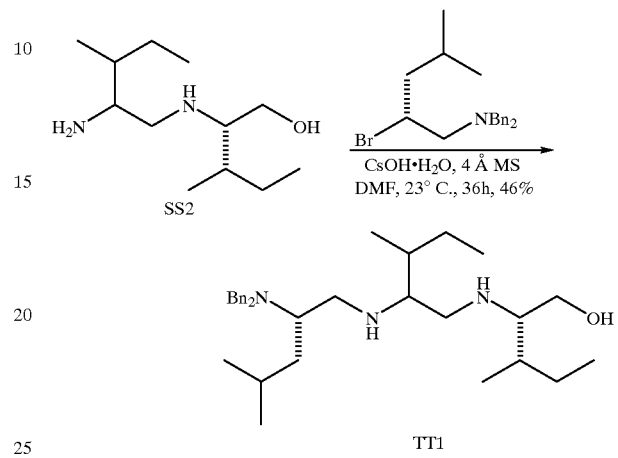

A flame dried 50 mL round-bottomed flask containing a magnetic stirring bar, a rubber septum, is flushed with dry nitrogen and charged with dimer SS2 (181 mg, 0.84 mmol), activatived 4 Å molecular sieves (250 mg), and cesium hydroxide monohydrate (140 mg, 0.84 mmol, 1 eq.) are dissolved in anhydrous N,N-dimethylformamide (10 ml) and allowed to stir for 30 minutes at room temperature. N,N-dibenzylleucinol bromide (500 mg, 1.26 mmol, 1.5 eq.) is added to the white suspension with vigorous stirring. The reaction is allowed to proceed at ambient temperature for 36 hours. The reaction is then filtered and the undissolved solids are washed with ethyl acetate. The filtrate is concentrated by air, and the residue is purified using flash column chromatography (10% MeOH/CH$_2$Cl$_2$ (v/v)) which yielded the desired protected trimer TT1 as a yellow oil (190 mg, 46%). Data for TT1: $^1$H NMR (360 MHz, CDCl$_3$) δ 0.70–0.93 (m, 12 H), 1.07 (s, 6 H), 1.29 –1.42 (m, 8 H), 2.45–2.51 (m, 1 H), 2.73–2.76 (m, 1 H), 3.19 (s, 3 H), 3.39–3.47 (m, 6 H), 3.86 (AB, J=13.5 Hz, 2 H), 4.00 (AB, J=13.4 Hz, 2 H), 7.08–7.38 (m, 10 H).

EXAMPLE 57

Solid Phase Synthesis of Dimer (Ile—Ile)

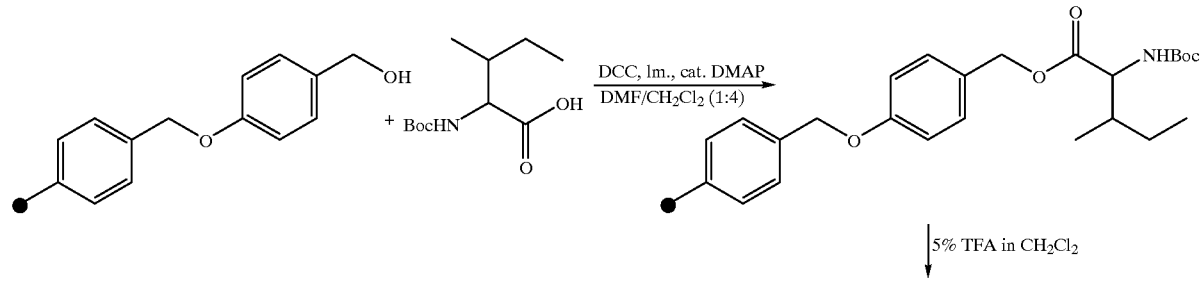

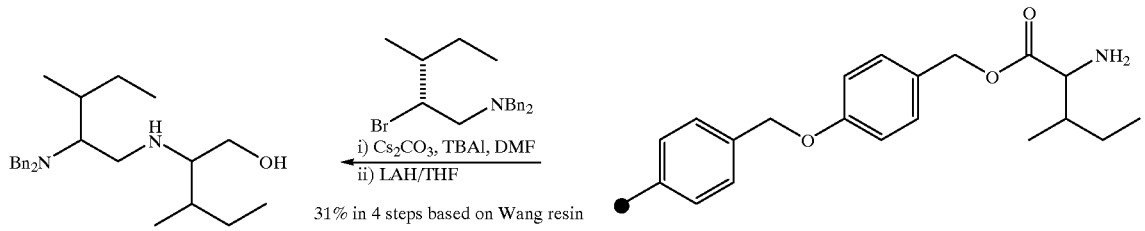

Alkoxide resin (1 g, 1.3 mmol) is esterified with tert-butoxycarbonyl protected isoleucine (930 mg, 4 mmol), DCC (825 mg, 4 mmol), imidazole (4 eq), and a catalytic amount of DMAP in a 1:4 mixture of DMF/CH$_2$Cl$_2$ at 0° C. to room temperature overnight. The resin is washed with H$_2$O, MeOH/H$_2$O, H$_2$O, THF, CH$_2$Cl$_2$, and MeOH, then dried under high vacuum. IR 3434, 3059, 3025, 2923, 1717, 1612, 1512, 1425, 1367, 1244, 1159, 1017, 758, 698, 542 cm$^{-1}$.

Boc-amino acid resin is treated with 5% TFA in CH$_2$Cl$_2$ at room temperature for 2 hours. Amino acid resin is filtered, washed with water, CH$_2$Cl$_2$, triethyl amine, ethanol, water, CHCl$_3$, and ether, then dired under high vacuum. The FT-IR spectrum exhibited a strong absorbance at 1738 cm$^{-1}$.

A flame dried 25 mL round-bottomed flask equipped with a magnetic stirring bar, is purged with dry nitrogen. Amino acid resin and cesium carbonate (1.3 g, 4 mmol) are dissolved in anhydrous N,N-dimethylforamide (10 mL), then the mixture is stirred for 30 minutes at room temperature. N,N-Dibenzylisoleucinyl bromide (1.44 g, 4 mmol) is added to the white suspension with vigorous stirring. The reaction is allowed to proceed at ambient temperatures for 48 h. The resin is washed with MeOH/H$_2$O, H$_2$O, 0.2 N HCl, H$_2$O, THF, CH$_2$Cl$_2$, and MeOH, then dried under high vacuum. The FT-IR spectrum exhibits a strong absorbance at 1738 cm$^{-1}$.

A flame dried 25 mL round-bottomed flask, equipped with a magnetic stirring bar, is charged with 20 mL of THF and N-alkylated-resin under an atmosphere of nitrogen. The suspension is cooled to 0° C., and 113 mg (3 mmol) of lithium aluminum hydride is added. The mixture is stirred for 7 hours at room temperature and cooled to 0° C. The mixture is carefully worked up by the dropwise and sequential addition of 0.1 mL of water, 0.1 mL of a 15% aqueous sodium hydroxide solution, and an 0.34 mL of water. The reaction mixture is filtered through coarse filtration frits to remove aluminum salts, and the latter are washed four times with 8 mL of diethyl ether. The combined filtrates are dried over sodium sulfate and concentrated under reduced pressure. The crude product is purified using flash chromatography (10:1 hexanes:EtOAc) to provide dialkylamine as a clear oil (154 mg, 31%). The trialkyamine is not observed.

EXAMPLE 58

Solid Phase Synthesis of Dimer (Ile-Leu)

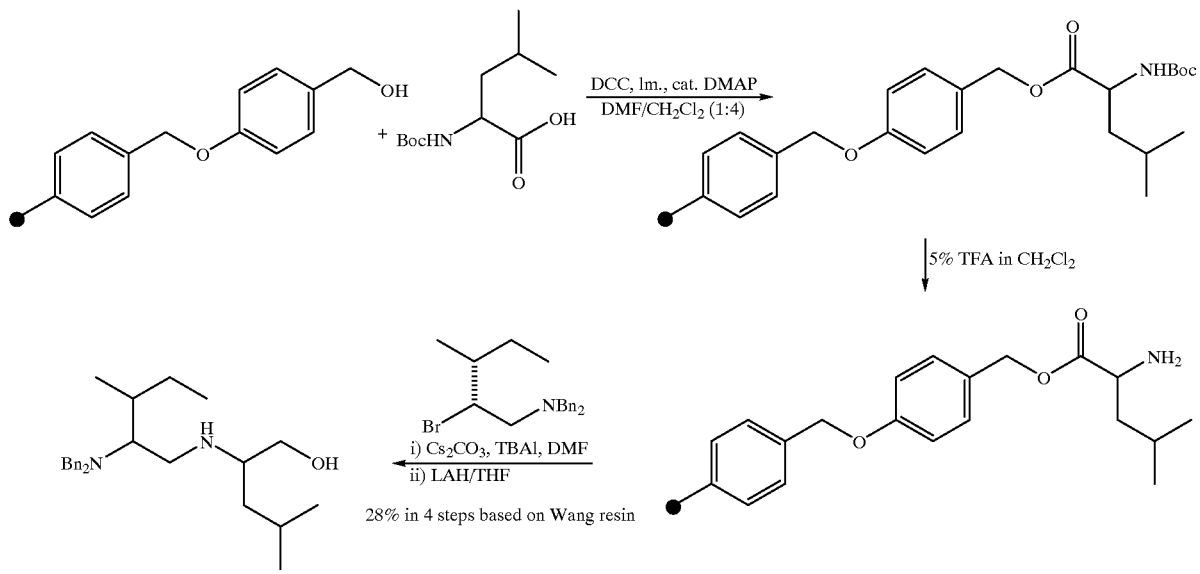

Alkoxide resin (1 g, 1.3 mmol) is esterified with tert-butoxycarbonyl protected leucine (930 mg, 4 mmol), DCC (825 mg, 4 mmol), imidazole (4 eq), and a catalytic amount of DMAP in a 1:4 mixture of DMF/$CH_2Cl_2$ at 0° C. to room temperature overnight. The resin is washed with $H_2O$, MeOH/$H_2O$, $H_2O$, THF, $CH_2Cl_2$, and MeOH, then dried under high vacuum. IR 3434, 3059, 3025, 2921, 2869, 1717, 1612, 1512, 1452, 1367, 15 1159, 1017, 758, 698, 542 $cm^{-1}$.

Boc-amino acid resin is treated with 5% TFA in $CH_2Cl_2$ at room temperature for 2 hours. Amino acid resin is filtered, washed with water, $CH_2Cl_2$, triethyl amine, ethanol, water, $CHCl_3$, and ether, then dired under high vacuum. The FT-IR spectrum exhibits a strong absorbance at 1743 $cm^{-1}$.

A flame dried 25 mL round-bottomed flask equipped with a magnetic stirring bar, is purged with dry nitrogen. Amino acid resin and cesium carbonate (1.3 g, 4 mmol) are dissolved in anhydrous N,N-dimethylforamide (10 mL), then the mixture is stirred for 30 minutes at room temperature. N,N-Dibenzylisoleucinyl bromide (1.44 g, 4 mmol) is added to the white suspension with vigorous stirring. The reaction is allowed to proceed at ambient temperatures for 48 h. The resin is washed with MeOH/$H_2O$, $H_2O$, 0.2 N HCl, $H_2O$, THF, $CH_2Cl_2$, and MeOH, then dried under high vacuum. The FT-IR spectrum exhibited a strong absorbance at 1749 $cm^{-1}$.

A flame dried 25 mL round-bottomed flask, equipped with a magnetic stirring bar, is charged with 20 mL of THF and N-alkylated-resin under an atmosphere of nitrogen. The suspension is cooled to 0° C., and 113 mg (3 mmol) of lithium aluminum hydride is added. The mixture is stirred for 7 hours at room temperature and cooled to 0° C. The mixture is carefully worked up by the dropwise and sequential addition of 0.1 mL of water, 0.1 mL of a 15% aqueous sodium hydroxide solution, and an 0.34 mL of water. The reaction mixture is filtered through coarse filtration frits to remove aluminum salts, and the latter are washed four times with 8 mL of diethyl ether. The combined filtrates are dried over sodium sulfate and concentrated under reduced pressure. The crude product is purified using flash chromatography (10:1 hexanes:EtOAc) to provide dialkylamine as a clear oil (139 mg, 28%). The trialkyamine is not observed.

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

What is claimed is:

1. A process providing a secondary amine of the general formula, R—NH—R', comprising:
    providing an organic electrophile, R—X, and a primary amine R'—$NH_2$, wherein R and R' each comprises the same or a different hydrocarbon having one or more carbon atoms and X comprises a leaving group, provided that the carbon atom covalently bonded to said leaving group and the carbon atom covalently bonded to said amine nitrogen atom are both saturated, and
    reacting said organic electrophile with said primary amine in an anhydrous solvent containing a cesium base in an amount sufficient to preferentially promote mono-N-alkylation of said primary amine by said organic electrophile, to provide a secondary amine.

2. The process as in claim 1, wherein said leaving group X is selected from the group consisting of chloride, bromide, iodide, O-Ms and O-Ts.

3. The process as in claim 1, wherein said solvent comprises a polar aprotic solvent.

4. The process of claim 1, wherein said solvent is selected from the group consisting of dimethyl sulfoxide, N,N-dimethylformamide, NMP, DMAC and mixtures thereof.

5. The process as in claim 1, further comprising removing water produced by said reaction of said organic electrophile with said primary amine.

6. The process as in claim 5, wherein removing water further comprises adding a molecular sieve having a pore size of about 3–5 Å.

7. The process as in claim 1, further comprising adding a halide-exchange promoting agent.

8. The process as in claim 7, wherein the halide-exchange promoting agent comprises tetrabutylammonium iodide.

9. The process as in claim 8, wherein about 0.1 to 2.0 moles of tetrabutylammonium iodide is added per mole of said primary amine.

10. The process as in claim 1, wherein said organic electrophile is covalently attached to an insoluble support matrix during reaction of said organic electrophile with said primary amine.

11. The process as in claim 10, wherein said insoluble support matrix comprises a Merrifield resin or Wang resin.

12. The process as in claim 1, wherein said primary amine is covalently bonded to an insoluble support matrix during reaction of said organic electrophile with said primary amine.

13. The process as in claim 12, wherein said insoluble support matrix comprises a Merrifield resin or a Wang resin.

14. The process as in claim 1, wherein said organic electrophile further comprises at least one chiral center, wherein each said chiral center is preserved during reaction of said organic electrophile with said primary amine.

15. The process as in claim 1, wherein said primary amine further comprises at least one chiral center, wherein each said chiral center is preserved during reaction of said organic electrophile with said primary amine.

16. The process as in claim 1, wherein said cesium base is selected from the group consisting of cesium carbonate, cesium bicarbonate, cesium hydroxide, and a mixture thereof.

17. A process for providing polyamines, comprising;
    providing an organic electrophile R—X wherein X is selected from the group consisting of chloride, bromide, iodide, O-Ts and O-Ms, and R comprises a hydrocarbon having 1–50 carbon atoms, provided that the carbon atom covalently bonded to X is saturated, and a primary amine R'—$NH_2$, wherein R' comprises a hydrocarbon having 1–50 carbon atoms, provided that the carbon atom covalently bonded to the amine nitrogen atom is saturated, and R' further comprises a thiol substituent, and
    reacting said organic electrophile with said primary amine in an anhydrous solvent comprising a cesium base in an amount sufficient to preferentially provide N-alkylated polyamine.

18. The process as in claim 17, wherein said primary amine is 2-aminoethanethiol hydrochloride.

19. The process as in claim 17, wherein said organic electrophile is 2-bromoethylamine hydrobromide.

20. The process as in claim 17, wherein said reaction further comprises adding a reaction-promoting amount of a molecular sieve with a pore size of about 3–5 Å.

21. The process as in claim 17, wherein said N-alkylated polyamine is N-(2-(2-aminoethylthio)ethyl) ethylenediamine.

22. The process as in claim 17, wherein said cesium base is selected from the group consisting of cesium carbonate, cesium bicarbonate, cesium bromide, cesium hydroxide, and mixtures thereof.

* * * * *

UNITED STATES PATENT AND TRADEMARK OFFICE
CERTIFICATE OF CORRECTION

PATENT NO.     : 6,423,871 B1
DATED           : July 23, 2002
INVENTOR(S)  : Kyung Woon Jung It is certified that error appears in the above-identified patent and that said Letters Patent is hereby corrected as shown below:

Column 5,
Lines 41-55,

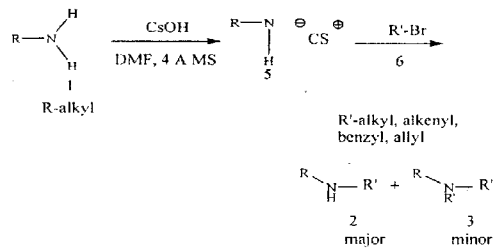

should read

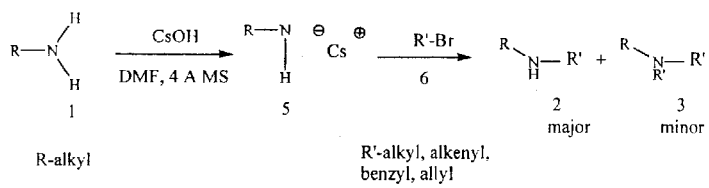

Column 29,
Line 41, "P1: $^H$ NMR (360 MHz, CDCl$_3$)" should read -- P1: $^1$H NMR (360 MHz, CDCl$_3$) --.

Column 41,
Line 65, "II1 II(209 mg, 70%)" should read -- II1 (209 mg, 70%) --.
Line 66, "2 (43 mg, 11%)" should read -- II2 (43 mg, 11%) --.

Signed and Sealed this

Thirteenth Day of January, 2004

JON W. DUDAS
*Acting Director of the United States Patent and Trademark Office*